US006635786B2

(12) United States Patent
Li et al.

(10) Patent No.: US 6,635,786 B2
(45) Date of Patent: Oct. 21, 2003

(54) SYMMETRICALLY DISUBSTITUTED AROMATIC COMPOUNDS AND PHARMACEUTICAL COMPOSITIONS FOR INHIBITING POLY (ADP-RIBOSE) GLYCOHYDROLASE, AND METHODS FOR THEIR USE

(75) Inventors: Jia-He Li, Cockeysville, MD (US); Dana Victor Ferraris, Towson, MD (US); Paul W. Kletzly, Arlington, VA (US); Weixing Li, Ellicott City, MD (US); Eric Yanjun Wang, Ellicott City, MD (US); Amy D. Xing, Ellicott City, MD (US); Weizheng Xu, Ellicott City, MD (US); Jie Zhang, Ellicott City, MD (US)

(73) Assignee: Guilford Pharmaceuticals, Inc., Baltimore, MD (US)

( * ) Notice: Subject to any disclaimer, the term of this patent is extended or adjusted under 35 U.S.C. 154(b) by 134 days.

(21) Appl. No.: 09/829,827

(22) Filed: Apr. 10, 2001

(65) Prior Publication Data

US 2002/0132852 A1 Sep. 19, 2002

Related U.S. Application Data

(60) Provisional application No. 60/261,738, filed on Jan. 16, 2001.

(51) Int. Cl.⁷ .............................................. C07C 233/00
(52) U.S. Cl. ........................ 564/158; 544/386; 544/387; 514/255; 514/617; 514/621
(58) Field of Search .......................... 564/158; 544/386, 544/387; 514/255, 617, 621

(56) References Cited

U.S. PATENT DOCUMENTS

| | | | |
|---|---|---|---|
| 3,817,992 A | 6/1974 | Sill et al. | 260/240.1 |
| 3,859,286 A | 1/1975 | Fleming et al. | 260/247.5 |
| 3,867,531 A | 2/1975 | Shemano | 424/248 |
| 3,890,328 A | 6/1975 | Palopoli et al. | 260/293.62 |
| 3,907,791 A | 9/1975 | Albrecht et al. | 260/246 |
| 3,937,833 A | 2/1976 | Shemano | 514/316 |
| 3,937,835 A | 2/1976 | Shemano | 424/275 |
| 3,947,593 A | 3/1976 | Shemano | 424/330 |
| 3,957,989 A | 5/1976 | Fleming et al. | 424/248 |
| 4,008,240 A | 2/1977 | Sill et al. | 260/293.58 |
| 4,041,165 A | 8/1977 | Shemano | 424/267 |
| 4,118,232 A | 10/1978 | Piller et al. | 96/99 |
| 5,521,160 A | * 5/1996 | Chucholowski et al. | |
| 5,587,384 A | 12/1996 | Zhang et al. | 514/309 |

FOREIGN PATENT DOCUMENTS

| | | |
|---|---|---|
| DE | 1950972 | 4/1970 |
| WO | WO 99/11645 | 3/1999 |

OTHER PUBLICATIONS

Sutcliffe et al., "The Synthesis and Properties of Dyes and Pigments Containing a 9,9'–Spirobifluorene Residue," *Journal of The Society of Dyers and Colourists*, 94, 306–309 (1978).
Cain et al., "Potential Antitumor Agents. IX. Bisquaternary Salts," *J. Med. Chem.*, 11, 963–966 (1968).
Ferranti et al., "Amidinoderivati Del 9H–Fluorene," *Farmaco, Ed., Sci.*, 37, 199–204 (1982).
Dünnwald et al., "Non–ionic Template Synthesis of Amide–linked Rotaxanes: Axles with Benzophenone and Cinnamic Acid Units," *Synthesis*, 3, 339–348 (1998).
Slama et al., "Specific Inhibition of Poly(ADP–ribose) Glycohydrolase by Adenosine Diphosphate (Hydroxymethyl)pyrrolidinediol", *J. Med. Chem.*, 38, 389–393 (1995).
Campbell et al., "The Friedel–Crafts Reaction of Fluoranthene", *J. Chem. Soc.*, 1404–1406 (1951).
Levine et al., *Toxicol. Appl. Pharmacol.*, 40, 137–145 (1977).
Schafer et al., *Cancer Chemother. Rp.*, 58, 821–827 (1974).
Alvarez–Gonzalez et al., *Mutat. Res.*, 218, 67–74 (1989).
Wachsman, *Mutat. Res.*, 350, 25–34 (1996).
Wielckens et al., *J. Biol. Chem.*, 257, 12872–12877 (1982).
Hatakeyama et al., *J. Biol. Chem.*, 261, 14902–14911 (1986).
Ha, *Neurobiology of Disease*, 7, 225–239 (2000).
Swanson et al., *NeuroReport*, 11, 1385–1388 (2000).
Ramsinghani et al., *Biochem.*, 37, 7801–7812 (1998).
Maruta et al., *Biochem.*, 30, 5907–5912 (1991).
Aoki et al., *Biochem. Biophys. Res. Comm.*, 210, 329–337 (1995).
Tsai et al., *Biochemistry Int'l*, 24, 889–897 (1991).
Uchiumi et al., *Biochem. Biophys. Res. Comm.*, 220, 411–417 (1996).
Tavassoli et al., *Biochim. Biophys. Acta*, 827, 228–234 (1985).
Albrecht et al., *J. Med. Chem.*, 17, 1150–1156 (1974).
Albrecht et al., *J. Med. Chem.*, 17, 886–889 (1974).
Wallis et al., *NeuroReport*, 5, 245–248 (1993).
Slama et al., *J. Med. Chem.*, 38, 4332–4336 (1995).
Aoki et al., *Biochim. Biophys. Acta*, 1158, 251–256 (1993).
Cosi et al., *Brain Research*, 809, 58–67 (1998).
Handrock, K. et al., *Toxicology*, 85, 199–213 (1993).
Hein et al., *Toxicology*, 58, 145–154 (1989).
Olofson, et al., *J. Org. Chem.*, 49, 2795–2799 (1984).
DiCioccio et al., *J. Natl. Cancer Inst.*, 60, 533–536 (1978).

\* cited by examiner

*Primary Examiner*—Paul J. Killos
(74) *Attorney, Agent, or Firm*—Merchant & Gould

(57) ABSTRACT

Symmetrically disubstituted aromatic compounds and pharmaceutical compositions containing such compounds that inhibit and/or modulate the activity of poly(ADP-ribose) glycohydrolase, also known as PARG, are described. The invention is also directed to the therapeutic or prophylactic use of such compounds and compositions, and to methods of treating diseases and disorders described herein, by administering effective amounts of such compounds.

26 Claims, No Drawings

SYMMETRICALLY DISUBSTITUTED AROMATIC COMPOUNDS AND PHARMACEUTICAL COMPOSITIONS FOR INHIBITING POLY (ADP-RIBOSE) GLYCOHYDROLASE, AND METHODS FOR THEIR USE

This invention claims the benefit of U.S. provisional patent application No. 60/261,738, filed Jan. 16, 2001.

The invention is directed to symmetrically disubstituted aromatic compounds and pharmaceutical compositions containing such compounds that inhibit and/or modulate the activity of poly(ADP-ribose) glycohydrolase, also known as PARG. The invention is also directed to the therapeutic or prophylactic use of such compounds and compositions, and to methods of treating diseases and disorders described herein, by administering effective amounts of such compounds.

A major focus of current biomedical research is on the mechanisms of cell death as new specific therapeutic agents that modulate these processes continue to be developed. Cell death is generally separated into two categories: apoptosis and necrosis. Apoptosis, commonly termed programmed cell death, is a genetically controlled process that follows physiologic stimuli in individual cells and typically involves ruffling of the cell membrane, nuclear and cytoplasmic condensation, intranucleosomal cleavage of DNA, and eventual phagocytosis of the cell without significant inflammation. Necrosis is a more rapid and severe process that occurs in groups of cells in response to pathologic injury. This mode of cell death is characterized by swelling of mitochondria and endoplasmic reticulum followed by a loss of membrane integrity and random destruction of DNA and other macromolecules culminating in substantial inflammatory response.

Although the vast majority of cell death literature suggests that all instances of cell death can be classified as apoptosis or necrosis, aspects of both mechanisms exist in a variety of cell death paradigms. To design rational therapeutic approaches to cell death, researchers should probably consider individual disease paradigms as occupying unique positions somewhere on a continuum between the extremes of apoptosis and necrosis.

The DNA repair enzyme poly (ADP-ribose) polymerase (PARP) has emerged as a major player along the continuum of cell death. When activated by DNA damage, PARP becomes the major consumer of NAD ($\beta$-nicotinamide adenine dinucleotide). Extensive PARP activation leads to severe depletion of NAD in cells suffering from massive DNA damage. Depletion of NAD, an important co-enzyme in energy metabolism, results in lower ATP production. As the cell consumes ATP in an effort to re-synthesize NAD, this energy crisis culminates in cell death.

After its activation by DNA strand breaks, PARP is believed to bind to damaged DNA and catalyze the synthesis and addition of long, branched chains of poly (ADP-ribose) (PAR) to a variety of nuclear proteins, including PARP itself, using NAD as substrate. PAR that is synthesized in response to massive DNA damage has a short half-life close to one minute as it is rapidly hydrolyzed at ribose-ribose bonds and converted to free ADP-ribose by poly(ADP-ribose) glycohydrolase (PARG), together with phosphodiesterase and (ADP-ribose) protein lyase. Alvarez-Gonzalez et al., *Mutat. Res.*, 218, 67–74 (1989); Wielckens et al., *J. Biol. Chem.*, 257, 12872 (1983). PARP and PARG constitute a cycle that converts a large amount of NAD to ADP-ribose. PARG is about 13- to 50-fold less abundant than PARP, but its specific catalytic activity is about 50- to 70-fold times higher so that there are no kinetic constraints in its ability to cope with large amount of PAR formed by PARP. Hatakeyama et al., *J. Biol. Chem.*, 261, 14902–14911 (1986). The rapid response of PARG to PAR synthesis indicates that PAR degradation is also an important nuclear response to DNA damage.

In less than an hour, overstimulation of PARP can cause a drop of NAD and ATP to less than 20% of the normal level. Berger, *Radiat. Res.*, 101, 4 (1985). Such a scenario is especially detrimental during ischemia when deprivation of oxygen has already drastically compromised cellular energy output. Calcium overload and subsequent free radical production during reperfusion are assumed to be a major cause of tissue damage. Part of the ATP drop, which is typical during ischemia and reperfusion, could be linked to NAD depletion due to poly(ADP-ribose) turnover. Endres et al., *J. Cereb. Blood Flow Metab.*, 17, 1143 (1997). Thus, by maintaining cellular NAD level, PARP inhibitors have therapeutic potential to rescue cells from ischemia and other oxidative stress. Preserving cellular energy level appears to be the main effect that PARP inhibitors exhibit in reducing necrotic cell death.

The conversion of PAR to free ADP-ribose by PARG could further promote PARP activity by providing additional substrate (ADP-ribose) for PARP and additional targets for poly(ADP-ribosyl)ation (sites where PARG has cleaved away ADP-ribose units). The activation of PARG thereby promotes the PARP-induced depletion of cellular energy, increased cell damage and cell death associated with the diseases and disorders linked to PARP activity. The rapid activation of PARG in response to PAR synthesis and PARP activation indicates that PAR degradation via PARG should promote the disorders and diseases associated with PARP activity. Although this is believed to be the mode of action, other mechanisms of action may be responsible for, or contribute to, the usefulness of PARG inhibitors including methods for treating or preventing the disorders or diseases described herein.

Accordingly, PARG inhibitors should be useful in down-regulating PARP by decreasing substrate and targets for PARP activity, and thus PARG inhibitors are useful for treating disorders and diseases associated with PARP activity. PARG inhibitors should be useful for any methods and therapies where the use of PARP inhibitors are utilized. See Ha, *Neurobiology of Disease*, 7, 225–239 (2000); Swanson et al., *NeuroReport*, 11, 1385–1388 (2000) (reporting results that "provide the first evidence that PARG inhibitors could be used to prevent oxidative cell death.").

Diseases implicated by PARP activation and the use of PARP inhibitors are known. For example, it has been reported that PARP activation plays a key role in both NMDA- and NO-induced neurotoxicity. See, e.g., Zhang et al., *Science*, 263, 687–689 (1994); Wallis, *NeuroReport*, 5, 245–248 (1993). The potential role of PARP inhibitors in treating neurodegenerative diseases and head trauma has been reported. See, e.g., Whalen et al., *J. Cereb. Blood Flow Metabol.*, 835–842 (1999); Endres et al., *J. Cereb. Blood Flow Metabol.*, 17, 1143–1151 (1997); Wallis et al., *Brain Res.*, 710, 169–177 (1996). It has been demonstrated that single injections of PARP inhibitors (3-aminobenzamide and 1,5-dihydroxyisoquinoline) have reduced the infarct size caused by ischemia and reperfusion of the heart or skeletal muscle in rabbits. Thiemermann et al., *Proc. Natl. Acad. Sci. USA*, 94, 679–683 (1997). PARP inhibitors are also proposed to play a role in the intestinal injury, cardiovascular failure, and multiple organ damage associated with resuscitated hemorrhagic shock. See, e.g., Liaudet et al., *Proc. Natl. Acad. Sci.*, 97, 10203–10208 (2000); Liaudet et al., *Shock*, 14, 134–141 (2000); McDonald et al., *Br. J. Pharm.*, 130, 843–850 (2000).

PARP activation has also been shown to provide an index following neurotoxic insults by glutamate (via NMDA receptor stimulation), reactive oxygen intermediates, amyloid β-protein, N-methyl-4-phenyl-1,2,3,6-tetrahydropyridine (MPTP) and its active metabolite N-methyl-4-phenylpyridine (MPP+), which participate in pathological conditions such as epilepsy, stroke, Alzheimer's disease, Parkinson's disease, Amyotrophic Lateral Sclerosis (ALS), Huntington's disease, schizophrenia, chronic pain, ischemia, and neuronal loss following hypoxia, hypoglycemia, ischemia, trauma, and nervous insult. See, e.g., U.S. Pat. No. 5,587,384 (using PARP inhibitors benzamide and 1,5-dihydroxy-isoquinoline to prevent NMDA-mediated neurotoxicity, and thus to treat stroke, Alzheimer's disease, Parkinson's disease, and Huntington's disease); WIPO International Publication Nos. WO 00/68206, 00/64878, 00/32579, and 00/67734 (using benzimidazole and phthalazine derivatives as inhibitors of PARP); Yang et al., *Shock*, 13, 60–66 (2000); Zhang et al., *J. Neurochem.*, 65, 1411–1414 (1995); Zhang et al., *Science*, 263, 687–689 (1994); Cosi et al., *Ann. N.Y. Acad. Sci.*, 825, 366–379 (1997); Cosi et al., *Brain Res.*, 809, 58–67 (1998); Dawson et al., *Cerebrovascular Disease*, 319–325 (1997); Dawson et al., *J. Neurosci.*, 16, 2479–2487 (1996); Iadecola, *Trends Neurosci.*, 20, 132–139 (1997).

PARP inhibitors have been reported to be effective in radiosensitizing hypoxic tumor cells and effective in preventing tumor cells from recovering from potentially lethal damage of DNA after radiation therapy, presumably by their ability to prevent DNA repair. See U.S. Pat. Nos. 5,032,617; 5,215,738; and 5,041,653. Evidence also exists that PARP inhibitors are useful for treating inflammatory bowel disorders, such as colitis (see, e.g., Zingarelli et al., *Gastroenterology*, 116, 335–345 (1999); Salzman et al., *Japanese J. Pharm.*, 75, 15 (1997); Southan et al., *Br. J. Pharm.*, 117, 619–632 (1996); Szabo et al., *J. Biol. Chem.*, 272, 9030–9036 (1997)), and in treating arthritis (see, e.g., Szabo et al., *Proc. Natl. Acad. Sci., USA*, 95, 3867–3872 (1998); Szabo et al., *Japanese J. Pharm.*, 75, 102 (1997)).

Furthermore, PARP inhibitors appear to be useful for treating hyperglycemia and diabetes (see Pieper et al., *Proc. Natl. Acad. Sci. USA*, 96, 3059–3064 (1999); Heller et al., *J. Biol. Chem.*, 270, 11176–11180 (1995)) and endotoxic or septic shock. See, e.g., Kuhnle et al., *Bio. Res. Comm.*, 263, 433–438 (1999); Oliver, *EMBO*, 18, 4446–4454 (1999); Zingarelli et al, *Shock*, 5, 258–264 (1996); Cuzzocrea, *Brit. J. Pharm.*, 122, 493–503 (1997). Yet another known use for PARP inhibitors is treating cancer. For example, U.S. Pat. No. 5,177,075 to Suto discusses several isoquinolines used for enhancing the lethal effects of ionizing radiation or chemotherapeutic agents on tumor cells. See also Suto et al, *Anticancer Drug Des.*, 7, 107–117 (1991); Weltin et al., *Oncol. Res.*, 6, 399–403 (1994). Still another use for PARP inhibitors is the treatment of peripheral nerve injuries, and the resultant pathological pain syndrome known as neuropathic pain, such as that induced by chronic constriction injury (CCI) of the common sciatic nerve and in which transsynaptic alteration of spinal cord dorsal horn characterized by hyperchromatosis of cytoplasm and nucleoplasm (so-called "dark" neurons) occurs. See Scott et al., *Ann Neurol*, 45, 120–124 (1999). PARP inhibitors have also been used to extend the lifespan and proliferative capacity of cells including treatment of diseases such as skin again, Alzheimer's disease, atherosclerosis, osteoarthritis, osteoporosis, muscular dystrophy, degenerative diseases of skeletal muscle involving replicative senescence, age-related macular degeneration, immune senescence, AIDS, and other immune senescence diseases, and to alter gene expression of senescent cells. See WIPO International Publication No. WO 98/27975; Barber et al., *Brain*, 122, 247–253 (1999).

PARG inhibitors should also provide similar therapeutic results that have been demonstrated with blocking PARP activity through the use of PARP inhibitors for each of the above-described diseases and disorders. The development of PARG inhibitors, however, lags significantly behind that of PARP inhibitors. Methods and compounds for inhibiting PARG are discussed in Tanuma et al, JP 042-75223-A2, JP 042-75296-A2, JP 032-05402-A2, JP 04-013684-A2; Ramsinghani et al., *Biochem.*, 37, 7801–7812 (1998); Slama et al., *J. Med. Chem.*, 38, 389–393 (1995); Slama et al., *J. Med. Chem.*, 38, 4332–4336 (1995); Maruta et al., *Biochem.*, 30, 5907–5912 (1991); Aoki et al., *Biochim. Biophys. Acta*, 1158, 251–256 (1993); Aoki et al., *Biochem. Biophys. Res. Comm.*, 210, 329–337 (1995); Tsai et al., *Biochemistry Int'l*, 24, 889–897 (1991); and Concha et al., *Biochemistry Int'l*, 24, 889–897 (1991).

PARG inhibitors are known to be effective for treating cancer as described by the Japanese Patents of Tanuma. However, in direct contrast to the present invention, evidence in the literature suggests that the mechanism of action for treating cancer by PARG inhibitors is that PARG inhibitors prevent the PARG-associated degradation of PAR that normally blocks the transcription and activation of oncogenes. The use of the PARG inhibitor tannic acid for treating HIV infection is discussed in Uchiumi et al., *Biochem. Biophys. Res. Comm.*, 220, 411–417 (1996). Several PARG inhibitors have been described in Tavassoli et al., *Biochim. Biophys. Acta*, 827, 228–234 (1985), including tilorone analogs (see Table I therein).

While not disclosing PARG inhibitors, U.S. Pat. Nos. 3,937,833 and 3,867,531 to Shemano disclose aromatic polycyclic compounds such as fluoranthene, fluorine, and fluoren-9-one, which are useful in treating conditions of delayed hypersensitivity. Similarly, use of substituted polycyclic aromatic compounds having potent antiviral activity are disclosed in U.S. Pat. No. 3,907,791; Albrecht et al., *J. Med. Chem.*, 17, 1150–1156; and Albrecht et al., *J. Med. Chem.*, 17, 886–889.

As recognized in the art, however, PARG represents a useful but little explored target for enzyme inhibition for therapeutic purposes. See Ha, *Neurobiology of Disease*, 7, 225–239 (2000). The known PARG inhibitors have had limited effect in reducing NMDA-receptor stimulation, or treating or preventing tissue damage resulting from cell damage or death due to necrosis or apoptosis, or treating or preventing neural tissue damage caused by NO; ischemia and reperfusion of the heart or skeletal muscle; neural tissue damage resulting from ischemia and reperfusion injury; neurological disorders and neurodegenerative diseases; in preventing or treating vascular stroke; in treating or preventing cardiovascular disorders; in treating other conditions and/or disorders such as age-related macular degeneration, immune senescence diseases, arthritis, atherosclerosis, cachexia, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, pain (such as neuropathic pain), renal failure, retinal ischemia, septic shock (such as endotoxic shock), resuscitated hemorrhagic shock, and skin aging;

in extending the lifespan and proliferative capacity of cells; in altering gene expression of senescent cells; or in radiosensitizing hypoxic tumor cells. Moreover, even the best-known PARP inhibitors have displayed unwanted metabolic side effects. See Milam et al., *Science*, 223, 589–591 (1984). Such considerations regarding side effects may also be concluded about PARG inhibitors.

There remains a need for compounds that modulate or inhibit PARG activity, compositions containing those compounds, and methods utilizing those compounds, wherein the compounds produce potent and reliable effects with fewer side effects, with respect to inhibiting PARG activity and treating the diseases and conditions described herein.

The present invention has addressed this need by the discovery of the symmetrically disubstituted aromatic compounds, pharmaceutically acceptable prodrugs, pharmaceutically active metabolites, and pharmaceutically acceptable salts thereof (such compounds, prodrugs, metabolites and salts are collectively referred to as "agents") described below, which modulate and/or inhibit the activity of the diseases or disorders described herein. Pharmaceutical compositions containing such agents are useful in treating diseases and disorders described herein due to free radical or reactive oxygen species induced cellular energy depletion and/or tissue damage resulting from cell damage or death.

In a general aspect, the invention relates to compounds of the Formula I:

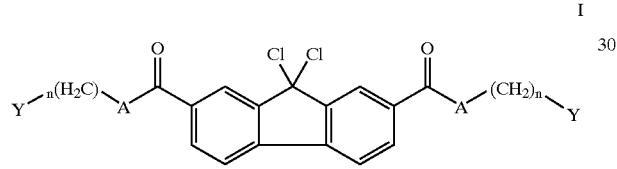

I wherein:
A is $CH_2$, O, or S;
n is 0 to 4; and
Y is hydrogen, or a substituted or unsubstituted cycloalkyl, aryl, or heteroaryl, or $N(R^1)(R^2)$, wherein $R^1$ and $R^2$ are independently hydrogen, a substituted or unsubstituted lower alkyl, lower alkenyl, heterocycloalkyl, alkoxy, aryloxy, alkylamino, arylamino, or $R^1$ and $R^2$ are taken together to form a substituted or unsubstituted five to seven membered heterocyclic ring that contains 1–3 heteroatoms of O, N, or S.

In a preferred embodiment, the invention relates to compounds having Formula I, wherein: A is O; n is 0–4; and Y is a substituted or unsubstituted aryl.

In another general aspect, the invention relates to compounds of the Formula II:

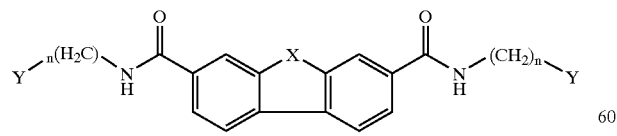

II wherein:
x is C=O, $CH_2$, or $C(Cl)_2$;
n is 0 to 4; and
Y is hydrogen, or a substituted or unsubstituted cycloalkyl, aryl, or heteroaryl, or $N(R^1)(R^2)$, wherein $R^1$ and $R^2$ are independently hydrogen, a substituted or unsubstituted lower alkyl, lower alkenyl, heterocycloalkyl, alkoxy, aryloxy, alkylamino, arylamino, or $R^1$ and $R^2$ are taken together to form a substituted or unsubstituted five to seven membered heterocyclic ring that contains 1–3 heteroatoms of O, N, or S.

In a preferred embodiment, the invention relates to compounds having Formula II, wherein: x is C=O or $C(Cl)_2$; n is 0 to 4; and Y is a substituted or unsubstituted aryl.

In another general aspect, the invention relates to compounds of the Formula III:

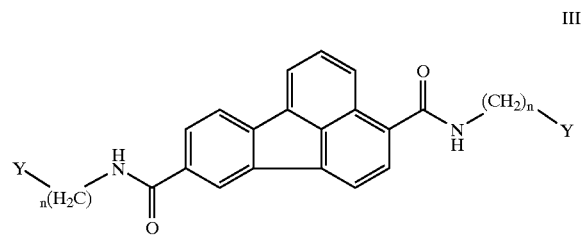

III wherein:
n is 0 to 4; and
Y is hydrogen, or a substituted or unsubstituted cycloalkyl, aryl, or heteroaryl, or $N(R^1)(R^2)$, wherein $R^1$ and $R^2$ are independently hydrogen, a substituted or unsubstituted lower alkyl, lower alkenyl, heterocycloalkyl, alkoxy, aryloxy, alkylamino, arylamino, or $R^1$ and $R^2$ are taken together to form a substituted or unsubstituted five to seven membered heterocyclic ring that contains 1–3 heteroatoms of O, N, or S.

In a preferred embodiment, the invention relates to compounds having Formula III, wherein: n is 0 to 4; and Y is a substituted or unsubstituted cycloalkyl, aryl, or heteroaryl, or $N(R^1)(R^2)$, wherein $R^1$ and $R^2$ are taken together to form a substituted or unsubstituted five or six membered heterocyclic ring that contains 1–3 heteroatoms of O, N, or S.

In another general aspect, the invention relates to compounds of the Formula IV:

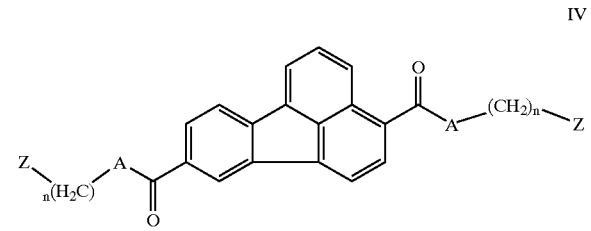

IV wherein:
n is 0 to 4;
A is $CH_2$, O, or S; and
Z is a substituted or unsubstituted aryl or heteroaryl, or $N(R^3)(R^4)$, wherein $R^3$ is a substituted or unsubstituted aryl or heteroaryl, and $R^4$ is hydrogen, a substituted or unsubstituted lower alkyl, lower alkenyl, heterocycloalkyl, alkoxy, aryloxy, alkylamino, arylamino, or $R^3$ and $R^4$ are taken together to form a substituted or unsubstituted five to six membered aromatic ring.

In a preferred embodiment, the invention relates to compounds having Formula IV, wherein: n is 1 to 3; A is $CH_2$ or O; and Z is a substituted or unsubstituted aryl or heteroaryl, or N(R³)(R⁴), wherein R³ is a substituted or unsubstituted aryl or heteroaryl, and R⁴ is a substituted or unsubstituted lower alkyl, or R³ and R⁴ are taken together to form a substituted or unsubstituted five to six membered aromatic ring.

In another general aspect, the invention relates to compounds of the Formula V:

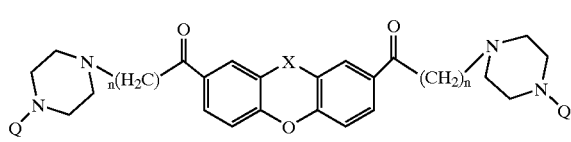

V wherein:
x is C=O, CH$_2$, or C(Cl)$_2$;
n is 0 to 4; and
Q is a substituted or unsubstituted aryl or heteroaryl.

In a preferred embodiment, the invention relates to compounds having Formula V, wherein: n is 2; x is C=O or CH$_2$; and Q is substituted or unsubstituted aryl.

In another general aspect, the invention relates to compounds of the Formula VI:

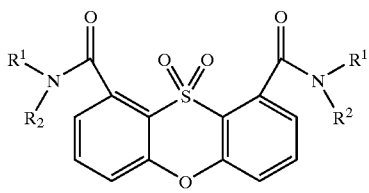

VI wherein:
R$^1$ and R$^2$ are independently hydrogen, a substituted or unsubstituted lower alkyl, lower alkenyl, heterocycloalkyl, alkoxy, aryloxy, alkylamino, arylamino, or R$^1$ and R$^2$ are taken together to form a substituted or unsubstituted five to seven membered heterocyclic ring that contains 1–3 heteroatoms of O, N, or S.

In a preferred embodiment, the invention relates to compounds having Formula VI, wherein: R$^1$ and R$^2$ are independently hydrogen, a substituted or unsubstituted lower alkyl, or R$^1$ and R$^2$ are taken together to form a substituted or unsubstituted six membered heterocyclic ring that contains 1–3 heteroatoms of O, N, or S.

In another general aspect, the invention relates to compounds of the Formula VII:

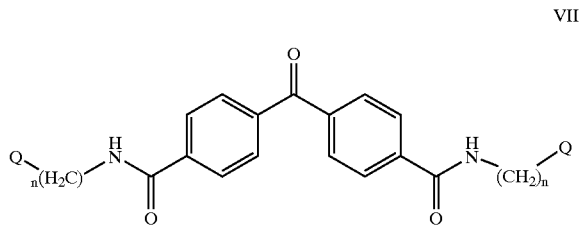

VII wherein:
n is 1 to 3; and
Q is a substituted or unsubstituted aryl or heteroaryl.

In another general aspect, the invention relates to compounds of the Formula VIII:

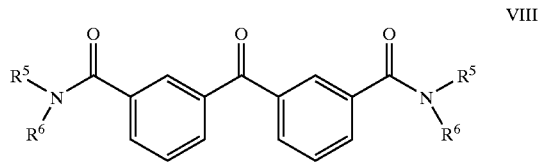

VIII wherein:
R$^5$ is hydrogen, and R$^6$ is a substituted or unsubstituted lower alkyl, lower alkenyl, heterocycloalkyl, alkoxy, aryloxy, alkylamino, arylamino, or R$^5$ and R$^6$ are taken together to form a substituted or unsubstituted five to seven membered heterocyclic ring that contains 1–3 heteroatoms of O, N, or S.

In a preferred embodiment, the invention relates to compounds having Formula VIII, wherein: R$^5$ is hydrogen, and R$^6$ is a substituted or unsubstituted lower alkyl, or R$^5$ and R$^6$ are taken together to form a substituted or unsubstituted six membered heterocyclic ring that contains 1–2 heteroatoms of N.

Preferred compounds of the invention are selected from:

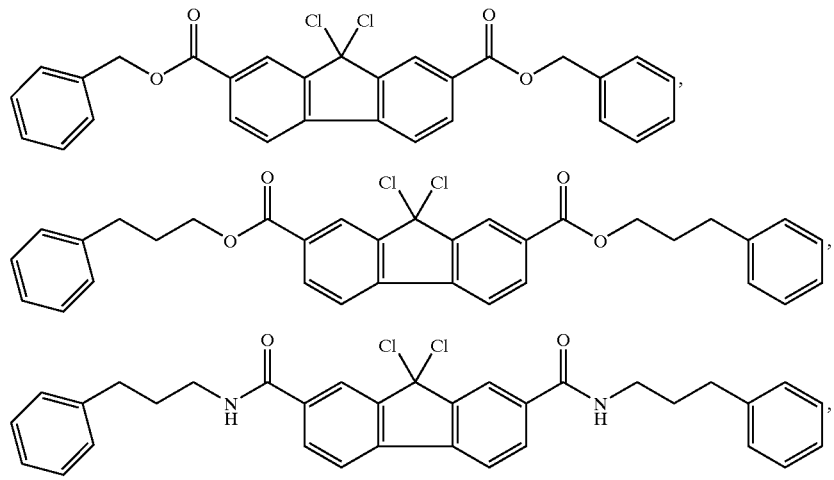

-continued
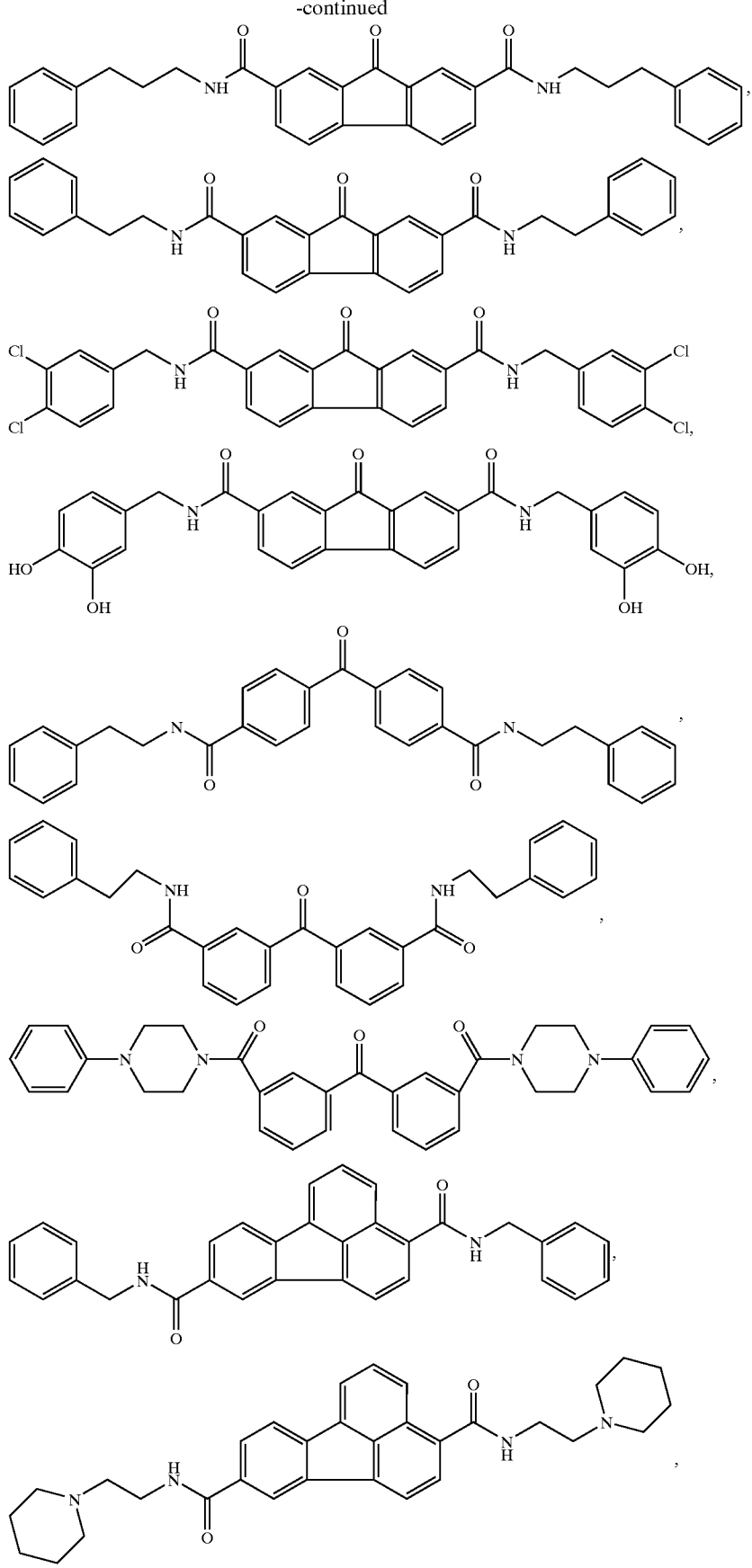

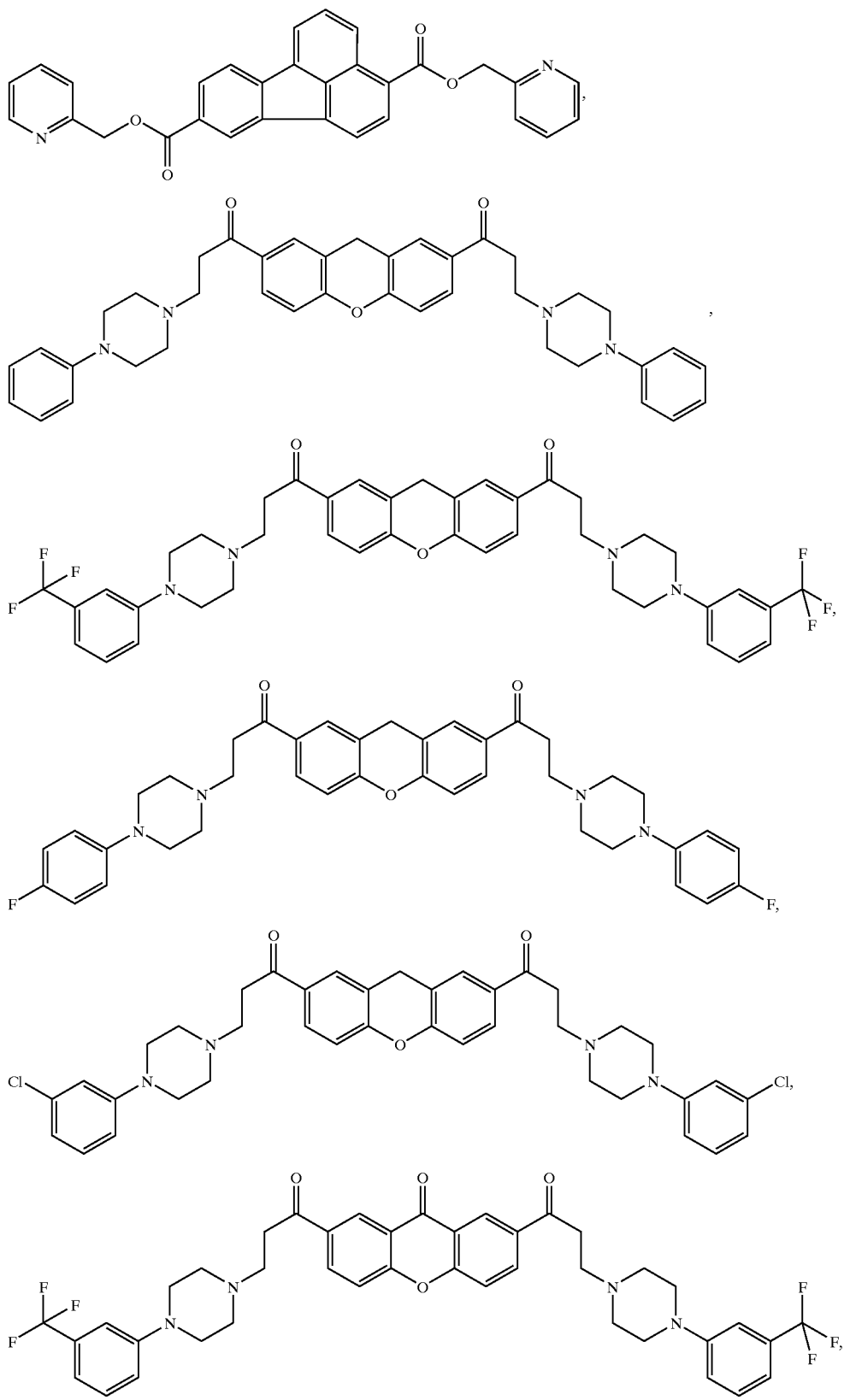

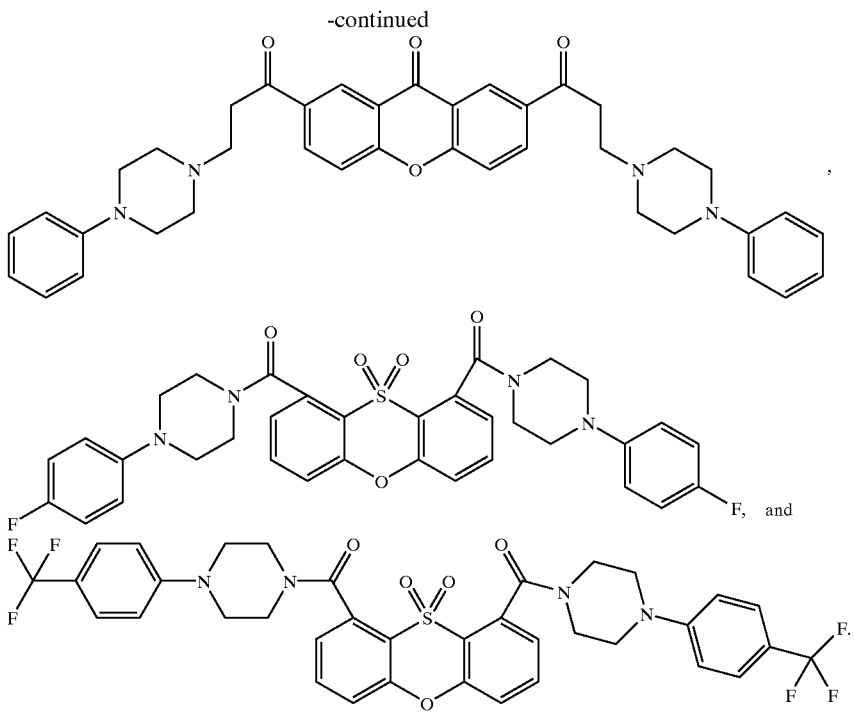

The invention is also directed to pharmaceutically acceptable prodrugs, pharmaceutically active metabolites, and pharmaceutically acceptable salts of the compounds or metabolites of Formulas I–VIII. Advantageous methods of making the compounds of Formulas I–VIII are also described.

The invention also relates to a method of modulating and/or inhibiting PARG by administering a compound of Formulas I–VIII or a pharmaceutically acceptable prodrug, pharmaceutically active metabolite, or pharmaceutically acceptable salt of such compound or metabolite thereof, to treat diseases and disorders including acute pain, arthritis, atherosclerosis, cachexia, cardiovascular disorders, chronic pain, degenerative diseases, diabetes, head trauma, hyperglycemia, immune senescence, inflammatory bowel disorders, ischemia, macular degeneration, muscular dystrophy, tissue damage resulting from ischemia and reperfusion injury, neurological disorders and neurodegenerative diseases, neuronal tissue damage or disease, neuropathic pain, nervous insult, osteoarthritis, osteoporosis, peripheral nerve injury, renal failure, resuscitated hemorrhagic shock, retinal ischemia, septic shock, skin aging, vascular stroke, diseases or disorders relating to lifespan or proliferative capacity of cells, and diseases or disease conditions induced or exacerbated by cellular senescence.

In a preferred embodiment, the invention relates to a method of modulating and/or inhibiting PARG by administering a compound of Formulas I–VIII or a pharmaceutically acceptable prodrug, pharmaceutically active metabolite, or pharmaceutically acceptable salt of such compound or metabolite thereof, to treat diseases and disorders including diabetes, head trauma, inflammatory bowel disorders, ischemia, tissue damage resulting from ischemia and reperfusion injury, neurological disorders and neurodegenerative diseases, neuronal tissue damage disease, neuropathic pain, nervous insult, peripheral nerve injury, retinal ischemia, vascular stroke, and diseases or disorders relating to lifespan or proliferative capacity of cells. Particularly preferred is a method as described immediately above wherein the disease or disorder is tissue damage resulting from ischemia and reperfusion injury.

The invention also relates to pharmaceutical compositions, each comprising an effective amount of an agent selected from compounds of Formulas I–VIII and pharmaceutically active metabolites, pharmaceutically acceptable prodrugs, and pharmaceutically acceptable salts of such compounds and metabolites, and a pharmaceutically acceptable carrier or vehicle for such agent. The invention further provides methods of treating diseases and disorders described herein due to free radical or reactive oxygen species induced cellular energy depletion and/or tissue damage resulting from cell damage or death, comprising administering effective amounts of one or more such agents to a patient in need of such treatment.

DETAILED DESCRIPTION OF THE INVENTION AND PREFERRED EMBODIMENTS

The inventive compounds Formulas I–VIII are useful for inhibiting free radical or reactive oxygen species induced cellular energy depletion, cell damage, or cell death and/or treating or preventing a disease or condition resulting from cell damage or death due to necrosis or apoptosis. In particular, the compounds of Formulas I–VIII, and pharmaceutically active metabolites, pharmaceutically acceptable prodrugs, and pharmaceutically acceptable salts of such compounds and metabolites, can be administered in effective amounts to treat or prevent specific diseases and disorders including acute pain, arthritis, atherosclerosis, cachexia, cardiovascular disorders, chronic pain, degenerative diseases, diabetes, head trauma, hyperglycemia, immune senescence, inflammatory bowel disorders, ischemia, macular degeneration, muscular dystrophy, tissue damage resulting from ischemia and reperfusion injury, neurological disorders and neurodegenerative diseases, neuronal tissue damage or disease, neuropathic pain, nervous insult, osteoarthritis, osteoporosis, peripheral nerve injury, renal failure, resuscitated hemorrhagic shock, retinal ischemia, septic shock, skin aging, vascular stroke, diseases or disorders relating to lifespan or proliferative capacity of cells, and diseases or disease conditions induced or exacerbated by cellular senescence.

The terms "comprising" and "including" are used herein in their open, non-limiting sense.

The term "alkyl" as used herein refers to straight- and branched-chain alkyl groups having one to twelve carbon atoms. Exemplary alkyl groups include methyl (Me), ethyl, n-propyl, isopropyl, butyl, isobutyl, sec-butyl, tert-butyl (tBu), pentyl, isopentyl, tert-pentyl, hexyl, isohexyl, and the like. The term "lower alkyl" designates an alkyl having from 1 to 6 carbon atoms (a $C_{1-6}$-alkyl). Exemplary substituted alkyls include fluoromethyl, difluoromethyl, trifluoromethyl, 2-fluoroethyl, 3-fluoropropyl, hydroxymethyl, 2-hydroxyethyl, 3-hydroxypropyl, and the like. Substituted alkyls are also represented by an alkyl substituted with, e.g., a substituted or unsubstituted cycloalkyl, heterocycloalkyl, aryl, or heteroaryl.

The term "alkenyl" refers to straight- and branched-chain alkenyl groups having from two to twelve carbon atoms. Illustrative alkenyl groups include prop-2-enyl, but-2-enyl, but-3-enyl, 2-methylprop-2-enyl, hex-2-enyl, and the like. The term "lower alkenyl" designates an alkenyl having from 1 to 6 carbon atoms (a $C_{1-6}$-alkenyl) The term "cycloalkyl" refers to saturated carbocycles having from three to twelve carbon atoms, including bicyclic and tricyclic cycloalkyl structures. Exemplary cycloalkyls include cyclopropyl, cyclobutyl, cyclopentyl, cyclohexyl, cycloheptyl, and the like.

A "heterocycloalkyl" group refers to a monocyclic radical containing carbon atoms, preferably 4 or 5 ring carbon atoms, and at least one heteroatom selected from nitrogen, oxygen and sulfur, and having partial or no unsaturation.

The terms "aryl" (Ar) and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like. Such moieties may be optionally substituted by one or more suitable substituents, for example, a substituent selected from a halogen (F, Cl, Br or I); lower alkyl; OH; $NO_2$; CN; $CO_2H$; O-lower alkyl; aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O.

The term "alkoxy" refers to the radical —O-alkyl. Illustrative examples include methoxy, ethoxy, propoxy, and the like.

The term "aryloxy" represents —O-aryl, wherein aryl is defined above.

The term "halogen" represents chlorine, fluorine, bromine or iodine. The term "halo" represents chloro, fluoro, bromo or iodo.

The term "alkylamino" represents —NHR where R is an alkyl group as defined above.

The term "arylamino" represents —NHAr where Ar is an aryl group as defined above.

The term "carboxy" refers to the radical —C(O) or C=O.

As indicated, the various moieties or functional groups for variables in the formulae may be optionally substituted by one or more suitable substituents. Exemplary substituents include a halogen (F, Cl, Br, or I), lower alkyl, —OH, —$NO_2$, —CN, —$CO_2H$, —O-lower alkyl, -aryl, -aryl-lower alkyl, —$CO_2CH_3$, —$CONH_2$, —$OCH_2CONH_2$, —$NH_2$, —$SO_2NH_2$, haloalkyl (e.g., —$CF_3$, —$CH_2CF_3$), —O—haloalkyl (e.g., —$OCF_3$, —$OCHF_2$), and the like.

The compounds of the invention may exhibit the phenomenon of tautomerism. While Formulas I–VIII cannot expressly depict all possible tautomeric forms, it is to be understood that Formulas I–VIII are intended to represent any tautomeric form of the depicted compound and are not to be limited merely to a specific compound form depicted by the formula drawings.

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the formulas are intended to cover solvated as well as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, acetic acid, or ethanolamine.

In addition to compounds of Formulas I–VIII, the invention includes pharmaceutically acceptable prodrugs, pharmaceutically active metabolites, and pharmaceutically acceptable salts of such compounds and metabolites.

"A pharmaceutically acceptable prodrug" is a compound that may be converted under physiological conditions or by solvolysis to the specified compound or to a pharmaceutically acceptable salt of such compound prior to exhibiting its pharmacological effect (s). Typically, the prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive PARG inhibitors using methods known in the art, such as those described by *Burger's Medicinal Chemistry and Drug Chemistry*, 1, 172–178, 949–982 (1995). See also Bertolini et al., *J. Med. Chem.*, 40, 2011–2016 (1997); Shan, et al., *J. Pharm. Sci.*, 86 (7), 765–767; Bagshawe, *Drug Dev. Res.*, 34, 220–230 (1995); Bodor, *Advances in Drug Res.*, 13, 224–331 (1984); Bundgaard, *Design of Prodrugs*

(Elsevier Press 1985); and Larsen, *Design and Application of Prodrugs,* Drug Design and Development (Krogsgaard-Larsen et al., eds., Harwood Academic Publishers, 1991).

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the PARG inhibitor, alter the way in which drugs are distributed in and excreted from the body. However, in some cases, metabolism of a drug is required for therapeutic effect. For example, anticancer drugs of the anti-metabolite class must be converted to their active forms after they have been transported into a cancer cell.

Since most drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products, or "metabolites," are more polar than the parent drugs, although a polar drug does sometime yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are transformed within the body to a more polar and more effective metabolite, p-hydroxyacetanilid (acetaminophen), which is widely used today. When a dose of acetanilide is given to a person, the successive metabolites peak and decay in the plasma sequentially. During the first hour, acetanilide is the principal plasma component. In the second hour, as the acetanilide level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

A further aspect of the present invention is directed to a pharmaceutical composition comprising a pharmaceutically acceptable carrier or a diluent and a therapeutically effective amount of a PARG inhibitor or a pharmaceutically acceptable salt, hydrate, ester, solvate, prodrug, metabolite, or stereoisomer.

PARG inhibitors are useful in the manufacture of pharmaceutical formulations comprising an effective amount thereof in conjunction with or as an admixture with excipients or carriers suitable for either enteral or parenteral application. As such, formulations of the present invention suitable for oral administration may be in the form of discrete units such as capsules, cachets, tablets, troche or lozenges, each containing a predetermined amount of the active ingredient; in the form of a powder or granules; in thee form of a solution or a suspension in an aqueous liquid or nonaqueous liquid; or in the form of an oil-in-water emulsion or a water-in-oil emulsion. The active ingredient may also be in the form of a bolus, electuary, or paste.

The composition will usually be formulated into a unit dosage form, such as a tablet, capsule, aqueous suspension or solution. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

Particularly preferred formulations include tablets and gelatin capsules comprising the active ingredient together with (a) diluents, such as lactose, dextrose, sucrose, mannitol, sorbitol, cellulose, dried corn starch, and glycine; and/or (b) lubricants, such as silica, talcum, stearic acid, its magnesium or calcium salt, and polyethylene glycol.

Tablets may also contain binders, such as magnesium aluminum silicate, starch paste, gelatin, tragacanth, methylcellulose, sodium carbosymethylcellulose and polyvinylpyrrolidone; carriers, such as lactose and corn starch; disintegrants, such as starches, agar, alginic acid or its sodium salt, and effervescent mixtures; and/or absorbents, colorants, flavors, and sweeteners. The compositions of the invention may be sterilized and/or contain adjuvants, such as preserving, stabilizing, swelling or emulsifying agents, solution promoters, salts for regulating osmotic pressure, and/or buffers. In addition, the composition may also contain other therapeutically valuable substances. Aqueous suspensions may contain emulsifying and suspending agents combined with the active ingredient. All oral dosage forms may further contain sweetening and/or flavoring and/or coloring agents.

These compositions are prepared according to conventional mixing, granulating, or coating methods, respectively, and contain about 0.1 to 75% of the active ingredient, preferably about 1 to 50% of the same. A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding, in a suitable machine, a mixture of the powdered active ingredient and a suitable carrier moistened with an inert liquid diluent.

When administered parenterally, the composition will normally be in a unit dosage, sterile injectable form (aqueous isotonic solution, suspension, or emulsion) with a pharmaceutically acceptable carrier. Such carriers are preferably non-toxic, parenterally-acceptable and contain non-therapeutic diluents or solvents. Examples of such carriers include water; aqueous solutions, such as saline (isotonic sodium chloride solution), Ringer's solution, dextrose solution, and Hanks' solution; and nonaqueous carriers, such as 1,3-butanediol, fixed oils (e.g., corn, cottonseed, peanut, sesame oil, and synthetic mono- or di-glyceride), ethyl oleate, and isopropyl myristate.

Oleaginous suspensions can be formulated according to techniques known in the art using suitable dispersing or wetting agents and suspending agents. Among the acceptable solvents or suspending mediums are sterile fixed oils. For this purpose, any bland fixed oil may be used. Fatty acids, such as oleic acid and its glyceride derivatives, including olive oil and castor oil, especially in their polyoxyethylated forms, are also useful in the preparation of injectables. These oil solutions or suspensions may also contain long-chain alcohol diluents or dispersants.

Sterile saline is a preferred carrier, and the compounds are often sufficiently water soluble to be made up as a solution for all foreseeable needs. The carrier may contain minor amounts of additives, such as substances that enhance solubility, isotonicity, and chemical stability, e.g., antioxidants, buffers and preservatives.

When administered rectally, the composition will usually be formulated into a unit dosage form such as a suppository or cachet. These compositions can be prepared by mixing the compound with suitable non-irritating excipients that are solid at room temperature, but liquid at rectal temperature, such that they will melt in the rectum to release the compound. Common excipients include cocoa butter, beeswax and polyethylene glycols or other fatty emulsions or suspensions.

Moreover, the compounds may be administered topically, especially when the conditions addressed for treatment involve areas or organs readily accessible by topical application, including neurological disorders of the eye, the skin or the lower intestinal tract.

For topical application to the eye, or ophthalmic use, the compounds can be formulated as micronized suspensions in isotonic, pH-adjusted sterile saline or, preferably, as a solution in isotonic, pH-adjusted sterile saline, either with or without a preservative such as benzylalkonium chloride. Alternatively, the compounds may be formulated into ointments, such as petrolatum.

For topical application to the skin, the compounds can be formulated into suitable ointments containing the compounds suspended or dissolved, for example, mixtures with one or more of the following: mineral oil, liquid petrolatum, white petrolatum, propylene glycol, polyoxyethylene compound, polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Topical application to the lower intestinal tract can be effected in rectal suppository formulations (see above) or in suitable enema formulations.

Formulations suitable for nasal or buccal administration (such as self-propelling powder dispensing formulations), may comprise about 0.1% to about 5% w/w of the active ingredient or, for example, about 1% w/w of the same. In addition, some formulations can be compounded into a sublingual troche or lozenge.

The formulations may conveniently be presented in unit dosage form and may be prepared by any of the methods well known in the art of pharmacy. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

In a preferred embodiment, the carrier is a solid biodegradable polymer or mixture of biodegradable polymers with appropriate time release characteristics and release kinetics. The composition of the invention may then be molded into a solid implant suitable for providing efficacious concentrations of the compounds of the invention over a prolonged period of time without the need for frequent redosing. The composition of the present invention can be incorporated into the biodegradable polymer or polymer mixture in any suitable manner known to one of ordinary skill in the art and may form a homogeneous matrix with the biodegradable polymer, or may be encapsulated in some way within the polymer, or may be molded into a solid implant. In one embodiment, the biodegradable polymer or polymer mixture is used to form a soft "depot" containing the pharmaceutical composition of the present invention that can be administered as a flowable liquid, for example, by injection, but which remains sufficiently viscous to maintain the pharmaceutical composition within the localized area around the injection site. The degradation time of the depot so formed can be varied from several days to a few years, depending upon the polymer selected and its molecular weight. By using a polymer composition in injectable form, even the need to make an incision maybe eliminated. In any event, a flexible or flowable delivery "depot" will adjust to the shape of the space it occupies within the body with a minimum of trauma to surrounding tissues.

The pharmaceutical composition of the present invention is used in amount that are therapeutically effective and the amounts used may depend upon the desire release profile, the concentration of the pharmaceutical composition required for the sensitizing effect, and the length of time that the pharmaceutical composition has to be released for treatment.

The PARG inhibitors of the invention are preferably administered as a capsule or tablet containing a single or divided dose of the compound, or as a sterile solution, suspension, or emulsion, for parenteral administration in a single or divided dose.

In another preferred embodiment, the PARG inhibitors of the invention can be prepared in lyophilized form. In this case, 1 to 100 mg of a PARG inhibitor may be lyophilized in individual vials, together with a carrier and a buffer, such as mannitol and sodium phosphate. Thee composition may then be reconstituted in the vials with bacteriostatic water before administration.

The compounds of the invention are used in the composition in amounts that are therapeutically effective. While the effective amount of the PARG inhibitor will depend upon the particular compound being used, amounts of these compounds varying from about 1% to about 65% have been easily incorporated into liquid or solid carrier delivery systems.

For medical use, the amount required of a PARG inhibitor to achieve a therapeutic effect will vary according to the particular compound administered, the route of administration, the mammal under treatment, and the particular disorder in disease concerned. A suitable systemic dose of a PARG inhibitor for a mammal suffering from, or likely to suffer from, any condition as described herein is typically in the range of about 0.1 to about 100 mg of base per kilogram of body weight. It is understood that the ordinarily skilled physician or veterinarian will readily be able to determine and prescribe the amount of the compound effective for the desired prophylactic or therapeutic treatment.

In so proceeding, the physician or veterinarian may employ an intravenous bolus followed by an intravenous infusion and repeated administrations, as considered appropriate. In the methods of the present invention, the compounds may be administered, for example, orally, parentally, in inhalation spray, topically, rectally, nasally, buccally, sublingually, vaginally, intraventricularly, or via an implanted reservoir in dosage formulations containing conventional non-toxic pharmaceutically-acceptable carriers, adjuvants and vehicles.

Parenteral includes, but is not limited to, the following examples of administration: intravenous, subcutaneous, intramuscular, intraspinal, intraosseous, intraperitoneal, intrathecal, intraventricular, intrasternal or intracranial injection and infusion techniques, such as by subdural pump. Invasive techniques are preferred, particularly direct administration to damaged neuronal tissue. While it is possible for the PARG inhibitor to be administered alone, it is preferable to provide it as part of a pharmaceutical formulation.

To be effective therapeutically as central nervous system targets, the compounds used in the methods of the present invention should readily penetrate the blood-brain barrier when peripherally administered. Compounds that cannot penetrate the blood-brain barrier, however, can still be effectively administered by an intraventricular route.

The compounds used in the methods of the present invention may be administered by a single dose, multiple discrete doses or continuous infusion. Since the compounds are small, easily diffusible and relatively stable, they are well suited to continuous infusion. Pump means, particularly subcutaneous or subdural pump means, are preferred for continuous infusion.

For the methods of the present invention, any effective administration regimen regulating the timing and sequence of doses may be used. Doses of the compounds preferably include pharmaceutical dosage units comprising an efficacious quantity of active compound. By an efficacious quantity is meant a quantity sufficient to inhibit PARG activity and/or derive the desired beneficial effects through administration of one or more of the pharmaceutical dosage units. In a particularly preferred embodiment, the dose is sufficient to prevent or reduce the effects of vascular stroke or other neurodegenerative diseases.

An exemplary daily dosage unit for a vertebrate host comprises an amount of from about 0.001 mg/kg to about 50 mg/kg. Typically, dosage levels on the order of about 0.1 mg to about 10,000 mg of the active ingredient compound are useful in the treatment of the above conditions, with preferred levels being about 0.1 mg to about 1,000 mg. The specific dose level for any particular patient will vary depending upon a variety of factors, including the activity of the specific compound employed; the age, body weight, general health, sex, and diet of the patient; the time of administration; the rate of excretion, any combination of the compound with other drugs; the severity of the particular disease being treated; and the form and route of administration. Typically, in vitro dosage-effect results provide useful guidance on the proper doses for patient administration. Studies in animal models can also be helpful. The considerations for determining the proper dose levels are well known in the art.

In methods of treating nervous insult (particularly acute ischemic stroke and global ischemia caused by drowning or head trauma), the compounds of the invention can be co-administered with one or more other therapeutic agents, preferably agents which can reduce the risk of stroke (such as aspirin) and, more preferably, agents which can reduce the risk of a second ischemic event (such as ticlopidine).

For methods of the invention, the term "preventing" refers to the ability of a compound or composition of the invention to prevent a disease identified herein in patients diagnosed as having the disease or who are at risk of developing such disease. The term also encompasses preventing further progression of the disease in patients who are already suffering from or have symptoms of such disease.

The term "treating" refers to:
(i) preventing a disease, disorder, or condition from occurring in an animal that may be predisposed to the disease, disorder and/or condition, but has not yet been diagnosed as having it;

(ii) inhibiting the disease, disorder, or condition, i.e., arresting its development; and (iii) relieving the disease, disorder, or condition, i.e., causing regression of the disease, disorder, and/or condition.

The compounds and compositions can be co-administered with one or more therapeutic agents either (i) together in a single formation, or (ii) separately in individual formulations designed for optimal release rates of their respective active agent. Each formulation may contain from about 0.01% to about 99.99% by weight, preferably from about 3.5% to about 60% by weight, of the compound of the invention, as well as one or more pharmaceutical excipients, such as wetting, emulsifying and pH buffering agents. When the compounds used in the methods of the invention are administered in combination with one or more other therapeutic agents, specific dose levels for those agents will depend upon considerations such as those identified above for compositions and methods of the invention in general.

For the methods of the present invention, any administration regimen regulating the timing and sequence of delivery of the compound can be used and repeated as necessary to effect treatment. Such regimen may include pretreatment and/or co-administration with additional therapeutic agents.

The inventive agents may be prepared using the reaction routes and synthesis schemes as described below, employing the general techniques known in the art using starting materials that are readily available. The preparation of preferred compounds of the present invention is described in detail in the following examples, but the artisan will recognize that the chemical reactions described may be readily adapted to prepare a number of other PARG inhibitors of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

PREPARATION OF COMPOUNDS AND EXAMPLES

In the examples described below, unless otherwise indicated all temperatures are set forth in degrees Celsius and all parts and percentages are by weight. Reagents were purchased from commercial suppliers such as Aldrich Chemical Company or Lancaster Synthesis Ltd. and were used without further purification unless otherwise indicated. Tetrahydrofuran (THF) and N,N-dimethylforamide (DMF) were purchased from Aldrich in Sure Seal bottles and used as received. All solvents were purified using standard methods known to those skilled in the art, unless otherwise indicated.

The reactions set forth below were done generally under a positive pressure of argon at an ambient temperature (unless otherwise stated) in anhydrous solvents, and the reaction flasks were fitted with rubber septa for the introduction of substrates and reagents via syringe. Glassware was oven dried and/or heat dried. Analytical thin layer chromatography (TLC) was performed on glass-backed silica gel 60 F 254 plates from Analtech (0.25 mm), eluted with the appropriate solvent ratios (v/v), and are denoted where appropriate. The reactions were assayed by TLC and terminated as judged by the consumption of starting material.

Visualization of the TLC plates was done with iodine vapor, ultraviolet illumination, 2% $Ce(NH_4)_4(SO_4)_4$ in 20% aqueous sulfuric acid, or p-anisaldehyde spray reagent, and activated with heat where appropriate. Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ and/or $Mg_2SO_4$ prior to filtration and evaporation of the solvents under reduced pressure on a rotary evaporator and noted as solvents removed in vacuo. Flash column chromatography (Still et al., *J. Org. Chem.*, 43, 2923 (1978)) was done using Merck silica gel (47–61 $\mu$m) with a silica gel crude material ratio of about 20:1 to 50:1, unless otherwise stated. Hydrogenolysis was done at the pressure indicated in the examples or at ambient pressure.

$^1$H-NMR spectra were recorded on a Bruker or Varian instrument operating at 400 MHz and $^{13}$C-NMR spectra were recorded operating at 75 MHz. NMR spectra were obtained as $CDCl_3$ solutions (reported in ppm), using chloroform as the reference standard (7.27 ppm and 77.00 ppm), $CD_3OD$ (3.4 and 4.8 ppm and 49.3 ppm), DMSO-$d_6$, or internally tetramethylsilane (0.00 ppm) when appropriate. Other NMR solvents were used as needed. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Infrared (IR) spectra were recorded on a Perkin-Elmer FT-IR Spectrometer as neat oils, as KBr pellets, or as $CDCl_3$ solutions, and when given are reported in wave numbers (cm$^{-1}$). The mass spectra were obtained using LSIMS, FAB, or electrospray. All melting points (mp) are uncorrected.

2,7-Disubstituted 9,9-dichlorofluorene derivatives of this invention are represented by Formulas I and II. As an example, the 9,9-dichlorofluorenes of this invention can be prepared in a conventional manner as illustrated below by Scheme 1.

Starting material, 9-fluorenone-2,7-dicarboxylic acid 1, is available from commercial sources. Chlorination of the diacids 1 with acyl halide reagents, such as thionyl chloride or $PCl_3$ provides 9,9-dicholorinated-bis-2,7-acyl chloride 2. The temperature of the reaction is between 0° C. and 200° C. For example, 2.0 gram of the diacid 1, 1 mL of DMF and 25 mL of thionyl chloride were placed into a flask and refluxed overnight. Excess thionyl chloride was removed in a vacuum to afford a yellowish solid, which was purified by recrystallization in toluene to give 1.5 g of compound 2 (56% yield). Amidation or etherification of compound 2 can be carried out conventionally by reaction of the acid chloride group of compound 2 with either an alcohol or amine compound to provide the desired ester or amide final product 3. Further details of this step can be found in General procedure B. Typical solvents include chlorinated solvents, various ethers, and dipolar aprotic solvents like DMF.

Scheme 1

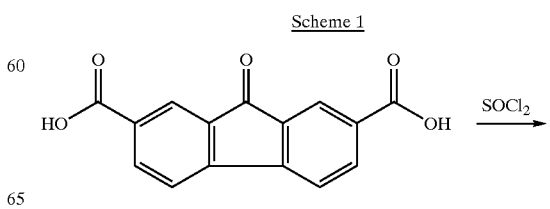

1

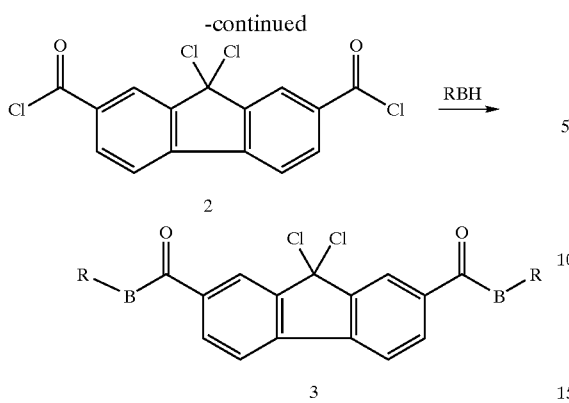

B = O,S or NH
R = substituted or unsubstituted alkyl, cycloalkyl, aryl, or heteroaryl Benzophenone-4,4'-dicarbamoyl derivatives of this invention are represented by Formula VII. These type of compounds can be prepared in a conventional manner as illustrated by Scheme 2.

Starting material, benzophenone-4,4'-dicarboxylic acid 4, is available from commercial sources. Chlorination of the diacids 4 with acyl halide reagents, such as thionyl chloride or $PCl_3$ provides benzophenone-4,4'-dicarboxylic acid chloride 5. Reacting the acyl chlorides of 5 with amine compounds gives the desired amides product 6. Further details of this step can be found in General procedures A and B.

Scheme 2

Benzophenone-3,3'-dicarbamoyl derivatives of this invention are represented by Formula VIII. Similar to the reaction described above in Scheme 2, these type of compounds can be prepared in a conventional manner as illustrated by Scheme 3.

Benzophenone-3,3'-dicarboxylic acid 8 can be prepared from 3,3'-bis(trifluoromethyl)bezophenone 7, which is available from commercial sources. Chlorination of the diacids 8 with acyl halide reagents, such as thionyl chloride or $PCl_3$ provides benzophenone-4,4'-dicarboxylic acid chloride 9. Reacting the acyl chlorides 9 with anime compounds gives the desired amides product 10. Further details of this step can be found in General procedures A and B.

Scheme 3

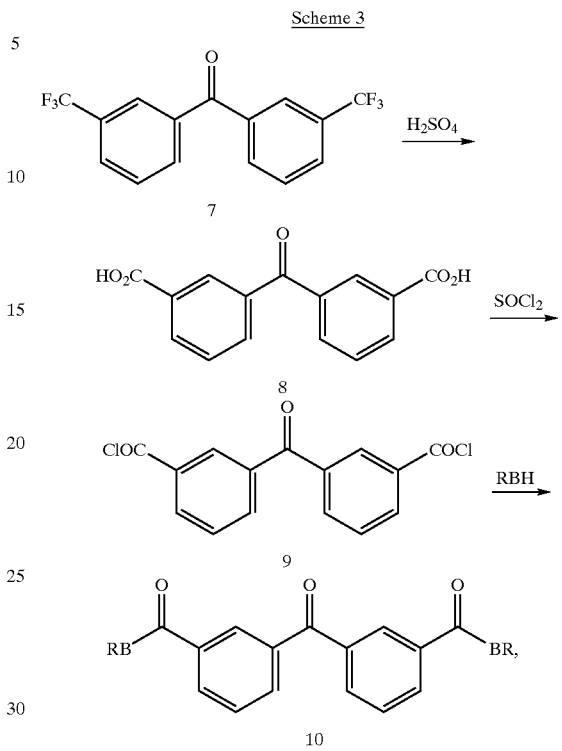

B = NH or O 3,9-Disubstituted fluoranthenecarbamoyl and carboxylate derivatives of this invention are represented by Formulas III and IV. These derivatives of this invention can be prepared in a conventional manner as illustrated by Scheme 4.

3,9-Diacetylfluoranthene 12 can be prepared from fluoranthene 11 according to known literature (Campbell et al., *J Chem. Soc.*, 1404–1406 (1951)). For example, to a mixture of fluoranthene (5.07 g, 24.6 mmol) and acetyl chloride (3.71 mL, 50.2 mmol, 2 eq.) in $CH_2Cl_2$ (100 mL) at 0° C. under $N_2$ was added portion wise $AlCl_3$ (8.2 g, 61.5 mmol) over a period of 1 h. The resulting mixture was stirred at 0° C. for 0.5 h, at room temperature for 20 h, and then was poured into ice-cold HCl (concentrated 5 mL/10 g ice). The resulting mixture was extracted with $CH_2Cl_2$ (3×30 mL). The combined organic layers were dried over $MgSO_4$ and filtered. The filtrate was collected and the solvent was removed in vacuo. The residue was purified on column chromatography (silica gel, 20–50% EtOAc/hexane) to give a light yellow crystalline (4.5 g, 64%). $^1H$ NMR ($CDCl_3$, 400 MHz) δ2.72 (s, 3H), 2.81 (s, 3H), 7.74 (t, J=12 Hz, 1H), 7.93 (d, J=8 Hz, 1H), 8.02 (m, 4H), 8.24 (d, J=8 Hz, 1H), 8.5 (s, 1H), 8.87 (d, J=8 Hz, 1H).

3,9-Fluoranthenedicarboxylic acid 13 can be obtained by oxidation of the acetyl group using oxidizing reagents, such as $CrO_4H$, $MnO_2$, NaOCl or $NaIO_4$. For example, to a solution of bleach (30 mL) and NaOH (2N, 10 mL) was added dropwise a solution of 3,9-diacetylfluorathene 12 (0.92 g, 3.22 mmol) in 1,4-dioxane (45 mL). The resulting mixture was heated at 75° C. for 2.5 h and stirred at room temperature for overnight. After it was acidified to pH~1–2 with HCl, the solid precipitate was formed and collected by filtration. The solid was washed with H$_2$O (2×2 mL), CH$_2$Cl$_2$ (2×5 mL), then dried in vacuo to give a yellow solid 13 (0.88 g, 94%). $^1$H NMR (DMSO-d$_6$, 400 MHz) δ7.85 (t, J=8 Hz, 1H), 8.09 (d, J=8 Hz, 1H), 8.20 (d, J=8 Hz, 1H), 8.30 (d, J=8 Hz, 1H), 8.39 (d, J=8 Hz, 1H), 8.44 (d, J=8 Hz, 1H), 8.67 (s, 1H), 8.87 (d, J=8 Hz, 1H).

Chlorination of the diacids 13 with acyl halide reagents, such as thionyl chloride or PCl$_3$ provides desired acid chloride 14. Reacting the acyl chlorides of 14 with an alcohol or anime compound gives desired 3,9-disubstitutedfluoranthenecarbamoyl and carboxylate derivatives 15. Further details of these two steps can be found in General procedures A and B.

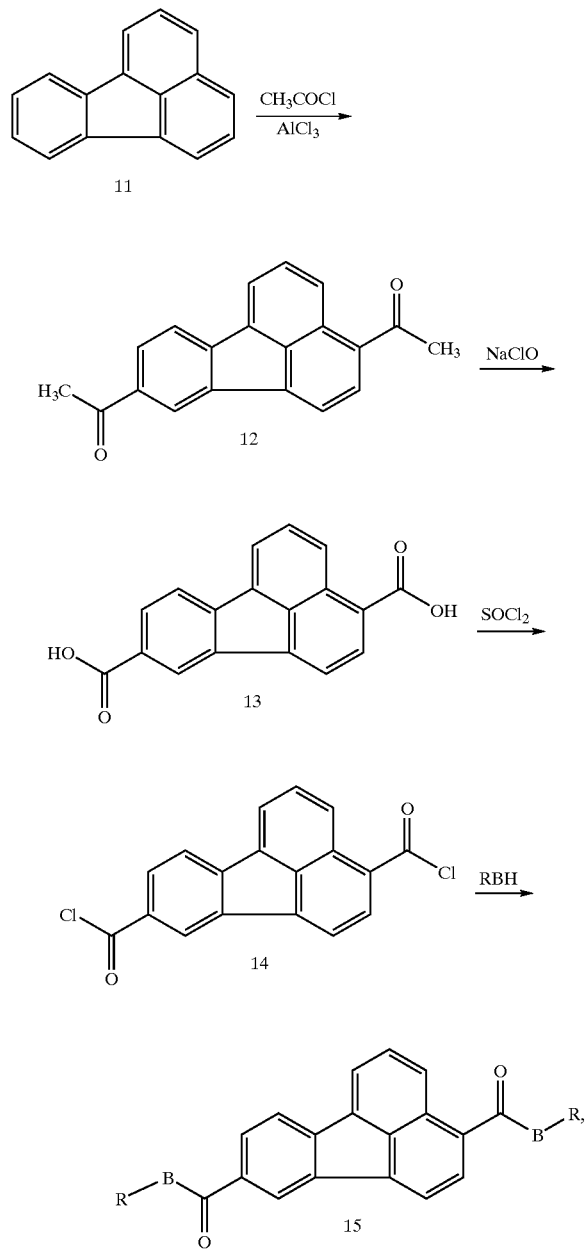

B = O or NH 2,7-Disubstituted xanthene and xanthenone derivatives of this invention are represented by Formula V. The 2,7-disubstituted xanthene and xanthene-9-ones of this invention can be prepared in a conventional manner as illustrated below schematically by Scheme 5.

2,7-Bis(3-chloro-propionyl)-xanthene 17 can be prepared from xanthene 16 through a Friedel-Crafts diacylation with 3-chloro-propionyl chloride. For example, to a mixture of xanthene (9.11 g, 50 mmol) and 3-chloro-propionyl chloride (11.9 mL, 130 mmol) in CH$_2$Cl$_2$ (200 mL) at −10° C. under N$_2$ was added AlCl$_3$ (14.7 g, 110 mmol) with rapid stirring. The resulting mixture was stirred at 0° C. for 0.5 h, at room temperature for 0.5 h, and then refluxed for 4 h. Upon cooling to room temperature, the mixture was poured into ice-water (50 mL), and sufficient dichloromethane was added to dissolve solids. The organic phase was washed with 2N HCl, water and brine, then dried over MgSO$_4$, and concentrated in vacuo to give a white solid, which was recrystallized from acetone/ethyl acetate to give product 17 (11.2 g, 62%). Mp 179–181° C. $^1$H NMR (CDCl$_3$, 400 MHz) δ7.86–7.84 (m, 4H), 7.13 (d, J=10 Hz, 2H), 4.18 (s, 2H), 3.94 (t, J=8 Hz, 4H), 3.44 (t, J=8 Hz, 4H). Anal. (C$_{19}$H$_{16}$Cl$_2$O$_3$. 0.1 H$_2$O).

Aminolysis of 2,7-bis(3-chloro-propionyl)-xanthene 17 with alkyl amino compounds provided desired 2,7-bis-(3-N-substituted-propionyl)-xanthenes 20. A typical reaction can be run with a desired alkyl amino compound in an organic solvent like tetrahydrofuran, butanone or ethanol in presence of KI. An example procedure is described in General Procedure C below. Using the same amidation condition, compounds 2,7-Bis-(3-piperidin-1-yl-propionyl)-xanthen-9-one 19 can be made from 2,7-Bis(3-chloro-propionyl)-xanthe-9-one 18.

Xanthe-9-one formation of compound 18 from xanthene derivative 17 can be achieved by conventional oxidation methods. Common oxidation reagents are oxygen gas, sodium dichromate, selenium oxide, pyridinium chlorochromate, pyridinium dichromate and Jones reagent. For example, chromium(VI) oxide (1.38 g, 0.014 mol) was gradually added to a solution of dichloromethane (30 mL) and pyridine (3.9 mL, 0.048 mol) and was stirred for 1 h. A solution of 17 (0.50 g, 0.14 mmol) in dichloromethane (15 mL) was added to above mixture and was stirred for 2 h. After addition of KHSO$_4$ (1.12 g, 8.2 mmol) to the solution and stirring for 1 h, the reaction mixture was filtered through a Celite with dichloromethane. The filtrate was washed with water and brine, dried over MgSO$_4$, and concentrated in vacuo to give a white solid, which was recrystallized from ethyl acetate to give product 18 (0.28 g, 54%).

Scheme 5

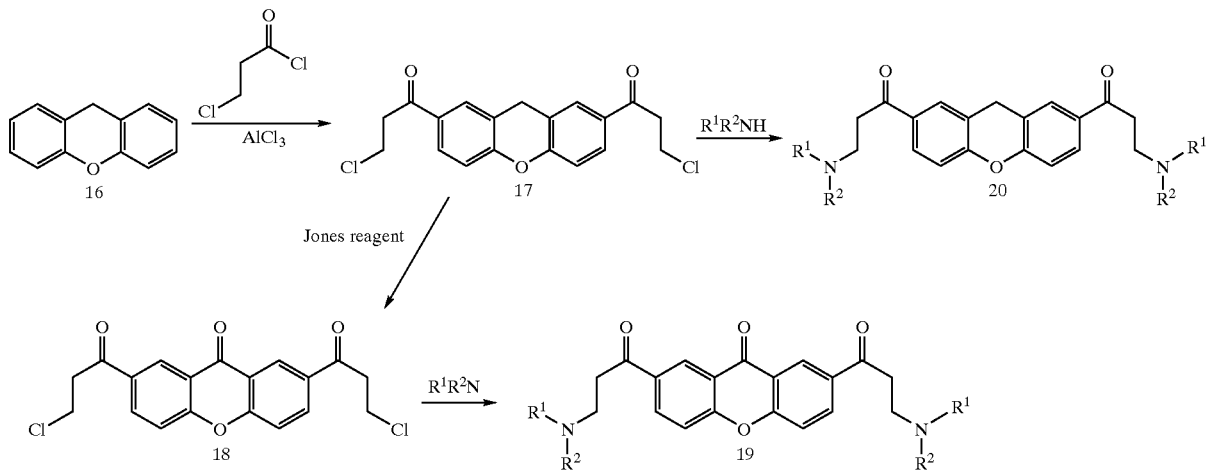

1,9-Bis(N-substituted)carbamoyl phenoxathiin-10,10-dioxide derivatives of this invention are represented by Formula VI. These type of compounds can be prepared in a conventional manner as illustrated by Scheme 6.

Chlorination of the diacids 21 using reagent of thionyl chloride or $PCl_3$ provides desired acid chloride 22. Reacting the acyl chlorides functionality of 22 with an amine compound gives desired 1,9-bis(N-substituted)carbamoylphenoxathiin-10,10-dioxide derivatives 23. Further details of these two steps can be found in General procedures A and B.

Scheme 6

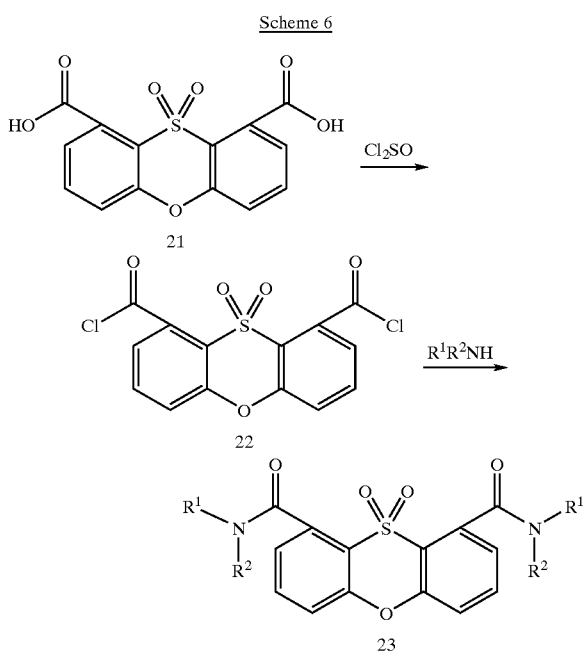

General Procedure A for the Preparation of Carboxylic Acid Chloride

A mixture of carboxylic diacids (25 mmol) and $SOCl_2$ (5 mL) in THF (10 mL) or DMF (5 mL) was refluxed under $N_2$ for 3 h. The excess $SOCl_2$ was removed in vacuo. The residue was mixed with a small amount of toluene (0.5 mL) and concentrated in vacuo. The residue was dried under vacuum for 2 h. The diacid chloride formed was used directly in the next step without any further purification.

General Procedure B for the Preparation of Amide

To a solution of amine or alcohol (3.0 mmol) and diisopropylethylamine (DIEA, 6.2 mmol) in THF (10 mL) was added a solution of the diacid chloride (1.0 mmol) in THF (1 mL). The resulting mixture was stirred at room temperature for overnight. The excess amine was removed by reacting with scavenge resin. The reaction mixture was filtered. The filtrate was concentrated in vacuo. The residue was purified on column chromatography (silica gel, 2–10% $MeOH/CH_2Cl_2$) to give pure amide or carboxylate.

Alternately, to a solution of amine or alcohol (2.5 mmol) and pyridine (0.5 mL) in DMF (5 mL) was added a solution of the diacid chloride (1.0 mmol) in THF (1 mL). The resulting mixture was stirred at room temperature for overnight and was poured into a saturated potassium carbonate solution. The organic layer was collected after extraction of the mixture with ethyl acetate (2×3 mL). The solvent was removed in vacuo and the residue was purified by column silica gel chromatography (6:1 hexanes/ethyl acetate) to afford the final amide or ester product. General yield is between 40 to 60%.

General Procedure C for the Preparation of 2,7-bis-(3-N-substituted-propionyl)-xanthenes and 2,7-bis-(3-N-substituted-propionyl)-xanthe-9-ones In a typical example, 2.0 eq. (mol) of triethyl amine was added to a stirred solution of 1.0 eq. (mol) of 17 or 18, and 2.2 eq. (mol) of secondary amine in acetonitrile (100 mL). The reaction mixture was heated to reflux overnight, and cooled to room temperature. The solvents were removed in vacuo. Dichloromethane (100 mL) was used to dissolve the residue and the solution was washed with water and brine, and dried over $MgSO_4$. Again the solvent was removed in vacuo. The resulting residue was suspended in small amount of diethyl ether and the precipitation was collected by filtration, washed with ether or ethyl acetate to give the desired product 17 or 18.

EXAMPLE 1

9,9-Dichloro-9H-fluorene-2,7-dicarboxylic acid bis-benzyl ester

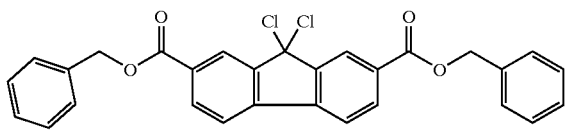

Prepared from 9,9-dicholorinated 2,7-diacyl chloride 2 and benzylic alcohol according to General Procedure A and B to give a solid (0.11 g, 39% yield). Mp 159–162° C. $^1$H-NMR (400 MHz, DMSO-$d_6$) δ8.53 (s, 1H), 8.43 (m, 2H), 7.71 (m, 2H), 7.74 (m, 3H), 5.6 (s, 2H). Anal. ($C_{29}H_{20}Cl_2O_4$).

EXAMPLE 2

9,9-Dichloro-9H-fluorene-2,7-dicarboxylic acid bis-(3-phenyl-propyl) ester

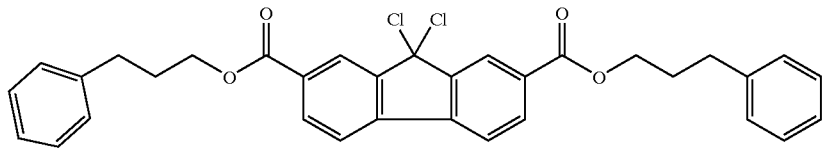

Prepared from 9,9-dicholorinated 2,7-diacyl chloride 2 and 3-phenyl-1-propanol according to General Procedure A and B to give a solid. Mp 91–92° C. $^1$H-NMR (400 MHz, DMSO-$d_6$) δ8.40 (s, 1H), 8.29 (m, 2H), 7.44 (m, 5H), 4.47 (m, 2H), 2.84 (m, 2H), 2.21 (m, 2H). Anal. ($C_{33}H_{28}Cl_2O_4$).

EXAMPLE 3

9,9-Dichloro-9H-fluorene-2,7-dicarboxylic acid bis-(3-phenyl-butyl) ester

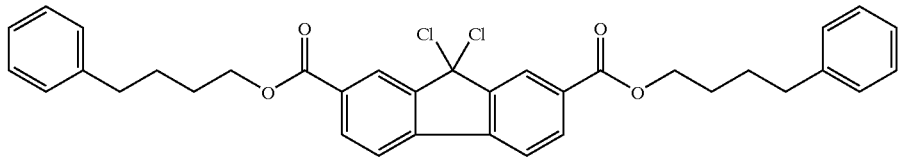

Example 3 was prepared by reacting 9,9-dicholorinated 2,7-diacyl chloride 2 with 4-phenylbutanol according to the procedure of Example 1 to provide the desired compound. LRMS (EI–), M–1=586.

Example 4

9,9-Dichloro-9H-fluorene-2,7-dicarboxylic acid bis-(p-fluorobenzyl) ester

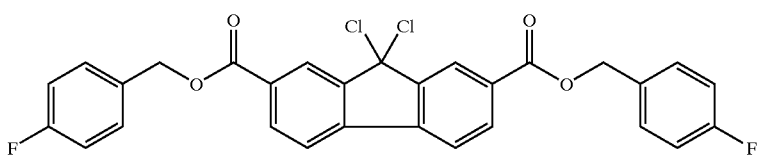

Example 4 was prepared by reacting 9,9-dicholorinated 2,7-diacyl chloride 2 with 4-fluorobenzylalcohol according to the procedure of Example 1 to provide the desired compound. LRMS (EI–), M–1=538.

EXAMPLE 5

9,9-Dichloro-9H-fluorene-2,7-dicarboxylic acid bis-(2-phenyl-ethyl) ester

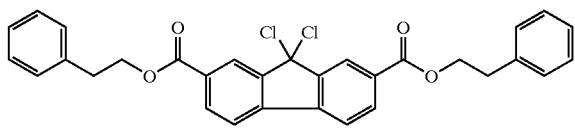

Example 5 was prepared by reacting 9,9-dicholorinated 2,7-diacyl chloride 2 with 2-phenylethanol according to the procedure of Example 1 to provide the desired compound. LRMS (EI–), M–1=530.

EXAMPLE 6

9,9-Dichloro-9H-fluorene-2,7-dicarboxylic acid bis-(3,4-dihydroxy-benzyl) ester

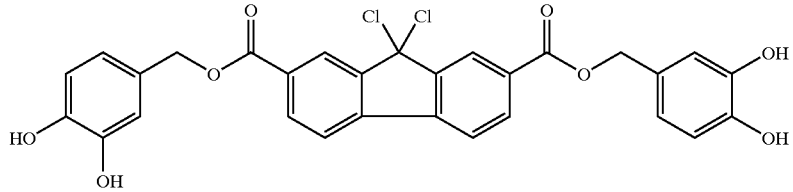

Example 6 was prepared by reacting 9,9-dicholorinated 2,7-diacyl chloride 2 with 3,4-dihydroxy-benzyl alcohol according to the procedure of Example 1 to provide the desired compound. LRMS (EI−), M−1=566.

EXAMPLE 7

9,9-Dichloro-9H-fluorene-2,7-dicarboxylic acid bis-methyl ester

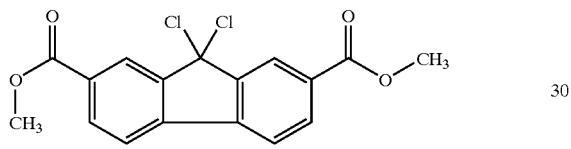

Example 7 was prepared by reacting 9,9-dicholorinated 2,7-diacyl chloride 2 with methanol according to the procedure of Example 1 to provide the desired compound. LRMS (EI−), M−1=350.

EXAMPLE 8

9,9-Dichloro-9H-fluorene-2,7-dicarboxylic acid bis-(2-naphthalen-1-yl-ethyl) ester

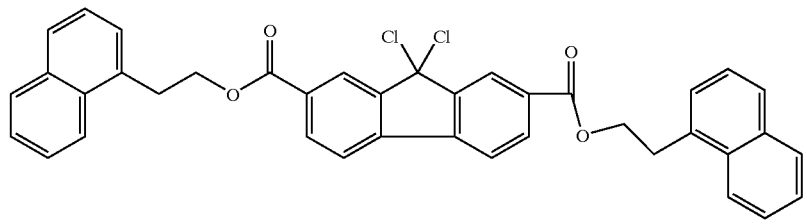

Example 8 was prepared by reacting 9,9-dicholorinated 2,7-diacyl chloride 2 with 2-naphthalen-1-yl-ethanol according to the procedure of Example 1 to provide the desired compound. LRMS (EI−), M−1=630.

EXAMPLE 9

9,9-Dichloro-9H-fluorene-2,7-dicarboxylic acid bis-(2-naphthalen-2-yl-ethyl) ester

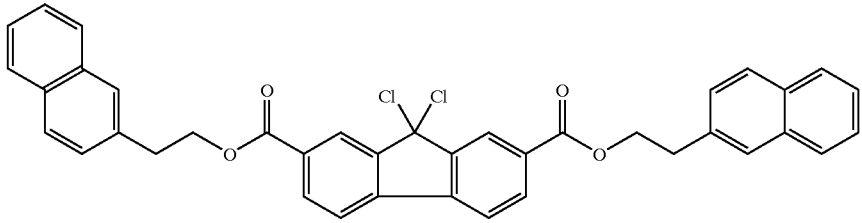

Example 9 was prepared by reacting 9,9-dicholorinated 2,7-diacyl chloride 2 with 2-naphthalen-2-yl-ethanol according to the procedure of Example 1 to provide the desired compound. LRMS (EI−), M−1=630.

EXAMPLE 10

9,9-Dichloro-9H-fluorene-2,7-dicarboxylic acid bis-(2-naphthalen-2-yl-methyl) ester

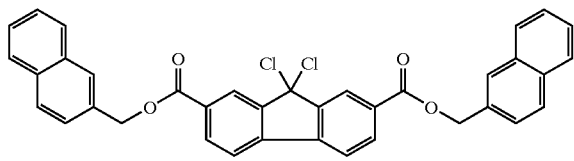

Example 10 was prepared by reacting 9,9-dicholorinated 2,7-diacyl chloride 2 with 2-naphthalen-2-yl-methanol according to the procedure of Example 1 to provide the desired compound. LRMS (EI−), M−1=618

EXAMPLE 11

9,9-Dichloro-9H-fluorene-2,7-dicarboxylic acid bis-(2-naphthalen-1-yl-methyl) ester Example 11 was prepared by reacting 9,9-dicholorinated 2,7-diacyl chloride 2 with 2-naphthalen-1-yl-methanol according to the procedure of Example 1 to provide the desired compound. LRMS (EI−), M−1=618.

EXAMPLE 12

9,9-Dichloro-9H-fluorene-2,7-dicarboxylic acid bis-[4-(4-methoxy-phenyl)-butyl]ester

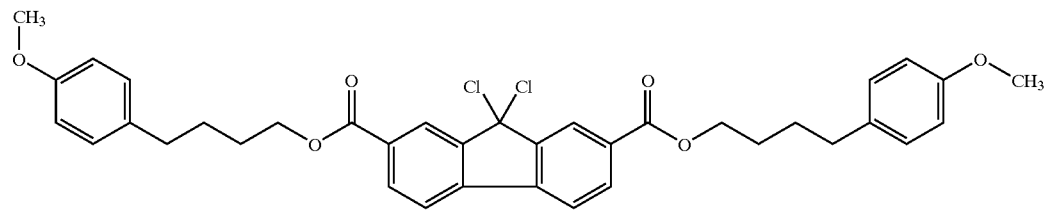

Example 12 was prepared by reacting 9,9-dicholorinated 2,7-diacyl chloride 2 with 4-(4-methoxy-phenyl)-butanol according to the procedure of Example 1 to provide the desired compound. LRMS (EI−), M−1=646.

EXAMPLE 13

2,7-Bis-[N-(3-phenyl-propyl)-carbamoyl]-9,9-dichloro-9H-fluorene

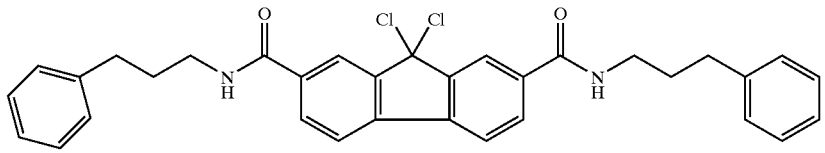

Prepared from 9,9-dicholorinated 2,7-diacyl chloride 2 and 3-phenylpropylamine according to General Procedure A and B to give a solid. Mp 165–167° C. $^1$H-NMR (400 MHz, CDCl$_3$) δ8.11 (s, 1H), 7.90 (d, J=9.6, 1H), 7.76 (d, J=8.4, 1H), 7.44 (m, 5H), 6.20 (m, 1H), 3.68 (m, 2H), 2.89 (t, J=7.2, 2H), 2.17 (m, 2H). Anal. ($C_{33}H_{30}Cl_2N_2O_2$).

EXAMPLE 14

2,7 Bis-[N-(naphthalen-1-ylmethyl)-carbamoyl]-9,9-dichloro-9H-fluorene

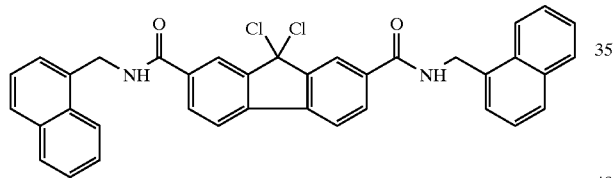

Example 14 was prepared by reacting 9,9-dicholorinated 2,7-diacyl chloride 2 with naphthalen-1-yl-methylamine according to the procedure of Example 13 to provide the desired compound. LRMS (EI+), M+Na=624.

EXAMPLE 15

2,7-Bis-[N-(phenethyl)-carbamoyl]-9,9-dichloro-9H-fluorene

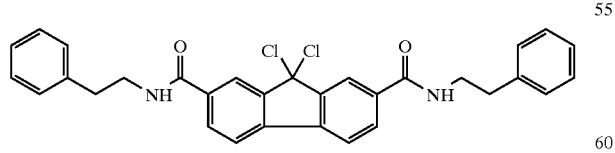

Example 15 was prepared by reacting 9,9-dicholorinated 2,7-diacyl chloride 2 with phenethylamine according to the procedure of Example 13 to provide the desired compound. LRMS (EI−), M−1=528.

EXAMPLE 16

2,7-Bis[N-(3-phenyl-propyl)carbamoyl])-9-Oxo-9H-fluorene

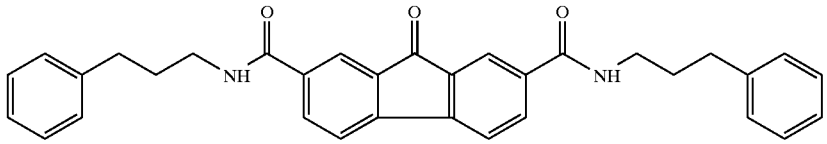

Prepared by amidation of 9-fluorenone-2,7-diacyl chloride using 3-phenpropyl amine according to General procedure B. 9-Fluorenone-2,7-diacyl chloride was prepared by reaction of 9-fluorenone-2,7-dicarboxylic acid 1 (2.0 g) in 5 mL of DMF and 25 mL of thionyl chloride at 50° C. for 10 h. The crude of 9-fluorenone-2,7-diacyl chloride was used for next step reaction without further purification. Mp 162–165° C. LRMS (EI−), M−1=501.

EXAMPLE 17

2,7-Bis(N-benzylcarbamoyl)-9-Oxo-9H-fluorene

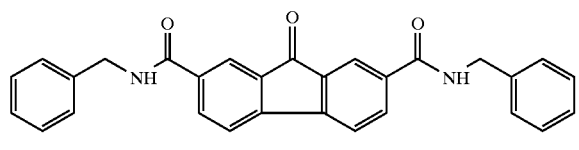

Prepared by reaction of 9-fluorenone-2,7-diacyl chloride with benzyl amine using the procedure of Example 16 provided the desired compound LRMS (EI−), M−1=586. LRMS (EI), M−1=445.

EXAMPLE 18

4,4'-Bis(N-phenethyl)carbamoyl-benzophenone

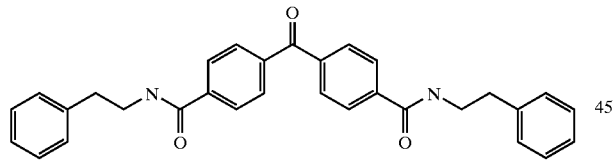

Prepared from benzophenone-4,4'-dicarboxylic acid chloride 9 and 2-phenyl-ethylamine according to General Procedure B to give a solid. Mp 244–248° C. $^1$H-NMR (400 MHz, DMSO-$d_6$) δ7.99 (d, 4H, J=8 Hz), 7.82 (d, 4H, J=8 Hz), 7.27 (m, 10H), 3.53 (m, 4H), 2.87 (m, 4H), Anal. ($C_{31}H_{28}N_2O_3$-0.25 $H_2O$).

EXAMPLE 19

4,4'-Bis(N-benzyl)carbamoyl-benzophenone

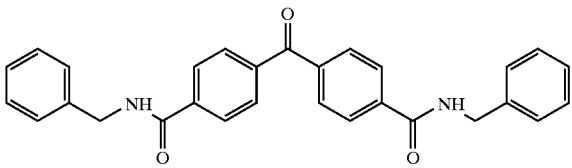

Example 19 was prepared by reacting benzophenone-4,4'-dicarboxylic acid chloride 5 and benzylamine according to General Procedure B to give a solid. LRMS (EI+), M+1=449.

EXAMPLE 20

4,4'-Bis(N-phenpropyl)carbamoyl-benzophenone

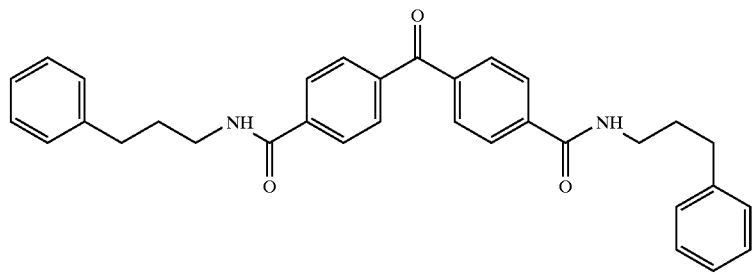

Example 20 was prepared by reacting benzophenone-4,4'-dicarboxylic acid chloride 5 and benzylamine according to General Procedure B to give a solid. LRMS (EI+), M+1=505.

EXAMPLE 21

3,3'-Bis(N-phenethyl)carbamoyl-benzophenone

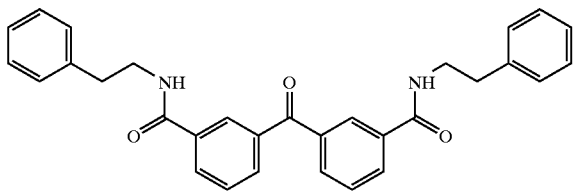

Prepared by reaction of benzophenone-3,3'-dicarboxylic acid chloride 9 and 2-phenethyl amine according to General Procedure B to give a solid. $^1$H-NMR (400 MHz, DMSO-$d_6$) δ8.80 (s, 1H), 8.19 (s, 1H), 8.14 (d, J=8.0 Hz, 1H), 7.88 (d, J=8.0 Hz, 1H), 7.24 (m, 4H), 5.76 (br s, 1H), 3.49 (m, 1H), 2.85 (m, 1H). LRMS: (ES+), M+1=477.

EXAMPLE 22

3,3'-Bis[N-(4-phenyl)-1-piperazine)carbamoyl]-benzophenone

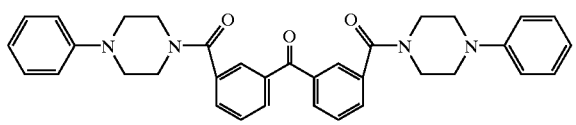

Prepared by reaction of benzophenone-3,3'-dicarboxylic acid chloride 9 and 4-phenyl)piperazine according to General Procedure B to give a white solid. Mp 157–158° C.

$^1$H-NMR (400 MHz, DMSO-$d_6$) δ7.87 (d, J=8.0 Hz, 1H), 7.78 (m, 2H), 7.69 (t, J=8.0 Hz, 1H), 7.23 (t, J=8.0 Hz, 2H), 6.95 (d, J=8.0 Hz, 2H), 6.81 (t, J=8.0 Hz, 1H), 3.77 (br s, 2H), 3.51 (br s, 2H), 3.21 (br s, 2H), 3.12 (br s, 2H). Anal. ($C_{35}H_{34}N_4O_3$-1.0$H_2O$).

EXAMPLE 23

3,9-Bis(N-phenylmethyl)fluoranthenedicarboxamide

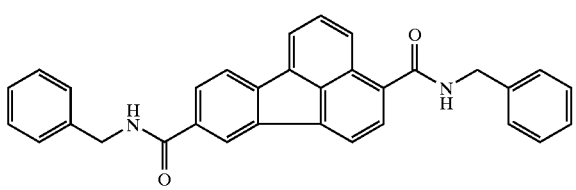

Prepared from acid chloride 14 and benzylic amine according to General Procedure B to give a solid. Mp 229–230.5° C. $^1$H NMR (DMSO-$d_6$, 400 MHz) δ4.35–4.45 (m, 4H), 7.05–7.30 (m, 10H), 7.60 (t, J=8 Hz, 1H), 7.80–7.85 (m, 2H), 7.99 (d, J=8 Hz, 1H), 8.04–8.09 (m, 2H), 8.18 (d, J=8 Hz, 1H), 8.44 (s, 1H), 9.04 (dt, J=24, 8 Hz, 2H).

EXAMPLE 24

3,9-Bis[N-(2-piperidin-1-yl)ethyl]fluoranthenedicarboxamide

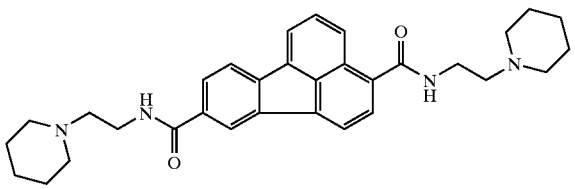

Prepared from acid chloride 14 and 2-N-pipyridine-ethylamine according to General Procedure B to give a solid. Mp 213–215.5° C. $^1$H NMR (MeOH-$d_4$, 400 MHz) δ1.35–1.65 (m, 12H), 2.5–2.62 (m, 8H), 2.66 (t, J=8 Hz, 4H), 3.50–3.62 (m, 4H), 7.62–7.66 (m, 1H), 7.84 (d, J=8 Hz, 2H), 7.95 (d, J=8 Hz, 1H), 7.98–8.03 (m, 2H), 8.27 (d, J=8 Hz, 1H), 8.36 (s, 1H).

EXAMPLE 25

3,9-Bis[N-(2-pyrrolidin-1-yl)-ethyl]fluoranthenedicarboxamide

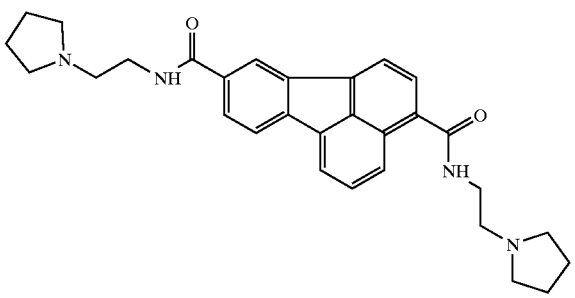

Prepared from acid chloride 14 and 2-(pyrrolidin-1-yl) ethyl amine according to General Procedure B to give a solid. LRMS (ES+), M+1=483.

EXAMPLE 26

3,9-Bis[N-(pyridin-3-yl)methyl]fluoranthenedicarboxamide

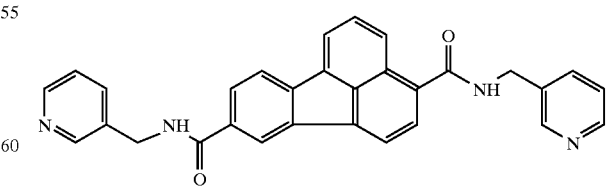

Prepared from acid chloride 14 and 3-aminomethyl pyridine according to General Procedure B to give a solid. LRMS (ES+), M+1=470.

EXAMPLE 27

3,9-Bis[N-(3-(morpholin-4-yl)propyl] fluoranthenedicarboxamide

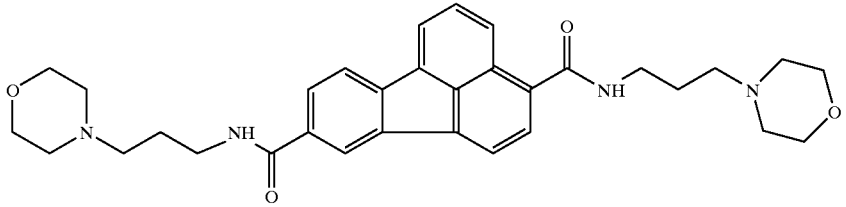

Prepared from acid chloride 14 and 3-(morpholin-4-yl) propyl amine according to General Procedure B to give a solid. LRMS (ES+), M+1=542.

EXAMPLE 28

3,9-Bis[N-(3,4-dimethoxy-benzyl)] fluoranthenedicarboxamide

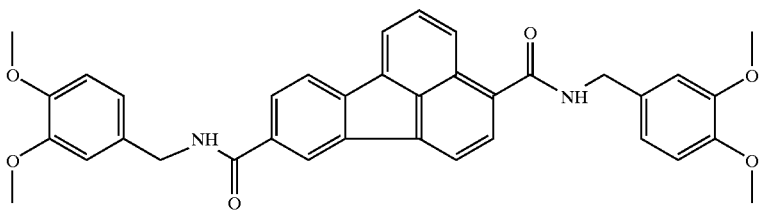

Prepared from acid chloride 14 and 3,4-dimethoxy-benzyl amine according to General Procedure B to give a solid. LRMS (ES−), M−1=588.

EXAMPLE 29

3,9-Bis[N-(2-phenoxy)ethyl] fluoranthenedicarboxamide

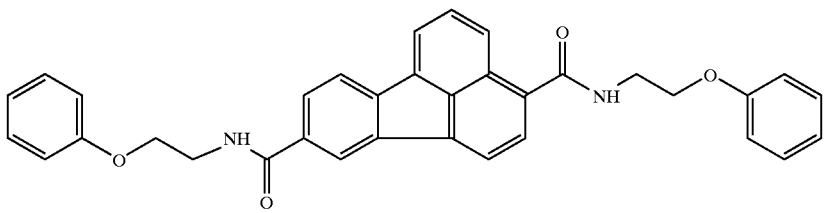

Prepared from acid chloride 14 and 2-(phenoxy)-ethyl amine according to General Procedure B to give a solid. LRMS (ES−), M−1=528.

EXAMPLE 30

3,9-Bis[N-[2-(2,4-dichloro-phenyl)]-ethyl] fluoranthenedicarboxamide

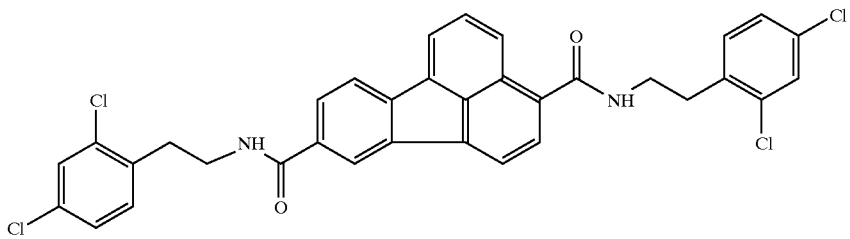

Prepared from acid chloride 14 and 2-(2,4-dichloro-phenyl)]-ethyl amine according to General Procedure B to give a solid. LRMS (ES−), M−1=634.

EXAMPLE 31

3,9-Bis{N-[(4-cyano-cyclohexyl)]methyl}fluoranthenedicarboxamide

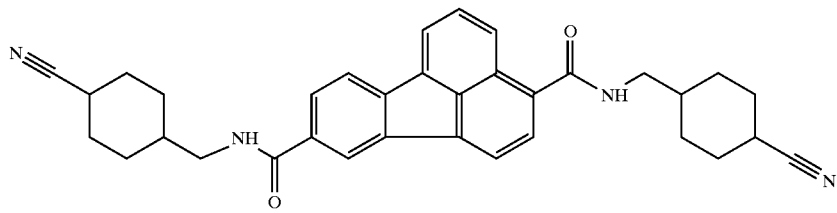

Prepared from acid chloride 14 and 4-(cyano-cyclohexyl) methyl amine according to General Procedure B to give a solid. LRMS (ES−), M−1=530.

EXAMPLE 32

3,9-Bis{N-[2-(2-methoxy-phenyl)]-ethyl}fluoranthenedicarboxamide

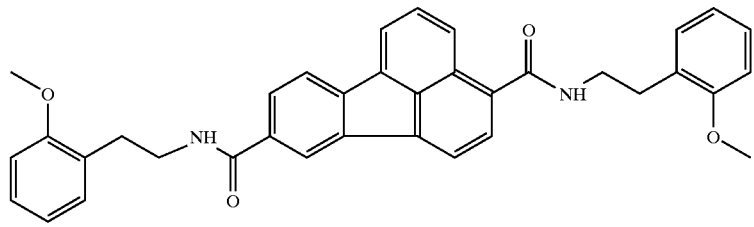

Prepared from acid chloride 14 and 2-(2-methoxyphenyl)]-ethyl amine according to General Procedure B to give a solid. LRMS (ES−), M−1=634.

EXAMPLE 33

3,9-Bis{N-[2-(3-methoxy-phenyl)]-ethyl}fluoranthenedicarboxamide

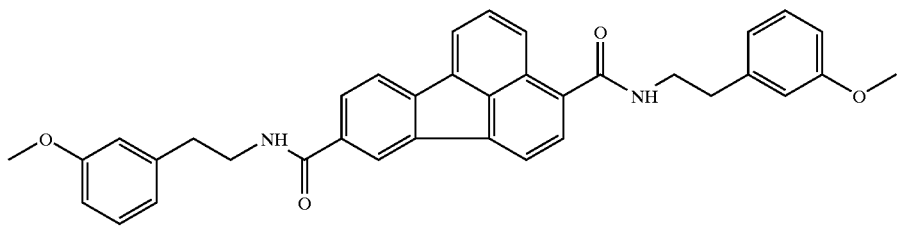

Prepared from acid chloride 14 and 2-(3-methoxyphenyl)]-ethyl amine according to General Procedure B to give a solid. LRMS (ES−), M−1=634.

EXAMPLE 34

3,9-Bis{N-[(2,3-dimethoxy-phenyl)]-methyl}fluoranthenedicarboxamide

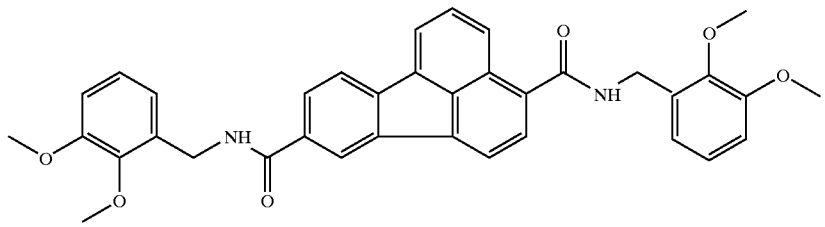

Prepared from acid chloride 14 and 2,3-dimethoxybenzyl amine according to General Procedure B to give a solid. LRMS (ES−), M−1=634.

EXAMPLE 35

3,9-Bis[N-[2-(4-sulfamoyl-phenyl)]-ethyl]fluoranthenedicarboxamide

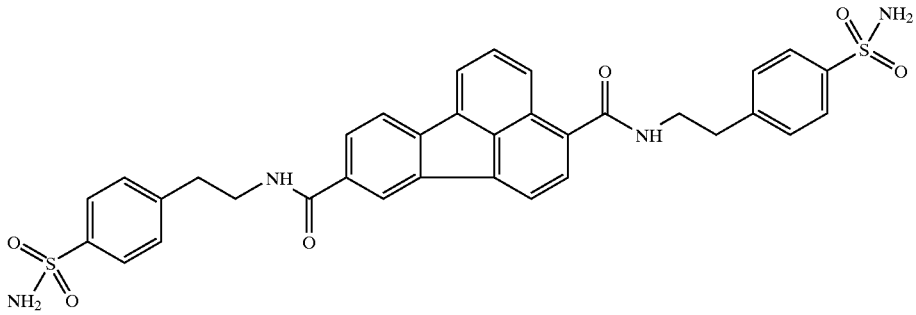

Prepared from acid chloride 14 and 4-(sulfamoylphenyl)-ethyl amine according to General Procedure B to give a solid. LRMS (ES−), M−1=634.

EXAMPLE 36

3,9-Bis(2-pyridinylmethyl)fluoranthenedicarboxylate

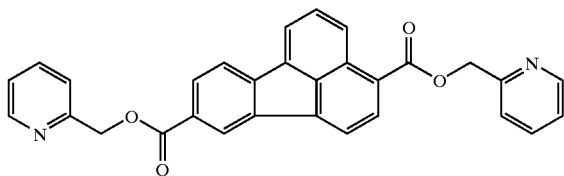

Prepared from acid chloride 14 and pyridine-2-methanol according to General Procedure B to give a solid. Mp 260° C. (dec.). $^1$H NMR (CDCl$_3$, 400 MHz) δ5.56 (s, 2H), 5.62 (s, 2H), 7.26–7.32 (m, 2H), 7.53 (t, J=8 Hz, 2H), 7.73–7.81 (m, 3H), 7.96 (d, J=8 Hz, 1H), 8.03 (t, J=8 Hz, 2H), 8.22 (d, J=8 Hz, 1H), 8.58 (d, J=8 Hz, 1H), 8.64–8.70 (m, 3H), 8.95 (d, J=8 Hz, 1H).

EXAMPLE 37

2,7-Bis-(3-chloro-propionyl)-xanthene

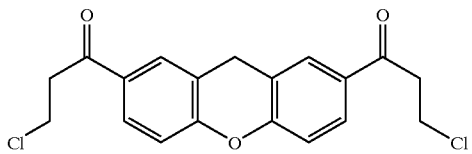

Prepared from xanthene 16 and 3-chloropropionyl chloride as described in Scheme 5 to give a solid. Mp 179–181° C. $^1$H NMR (CDCl$_3$, 400 MHz) δ7.86–7.84 (m, 4H), 7.13 (d, J=10 Hz, 2H), 4.18 (s, 2H), 3.94 (t, J=8 Hz, 4H), 3.44 (t, J=8 Hz, 4H). Anal. (C$_{19}$H$_{16}$Cl$_2$O$_3$. 0.1 H$_2$O).

EXAMPLE 38

2,7-Bis-(3-chloro-propionyl)-xanthen-9-one

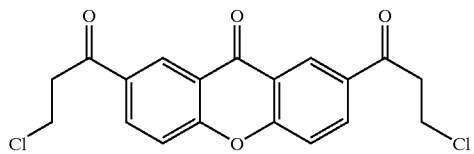

Prepared from the compound above (Example 37) to give a solid. Mp 174–176° C. $^1$H NMR (CDCl$_3$, 400 MHz) δ8.91 (d, J=2.3 Hz, 2H), 8.43 (dd, J=8.8, 2.3 Hz, 2H), 7.65 (d, J=8.8 Hz, 2H), 3.98 (t, J=6.5 Hz, 4H), 3.61 (t, J=6.5 Hz, 4H). Anal. (C$_{19}$H$_{11}$Cl$_2$O$_4$).

EXAMPLE 39

2,7-Bis-[3-(4-phenyl-piperazin-1-yl)propionyl]-xanthene

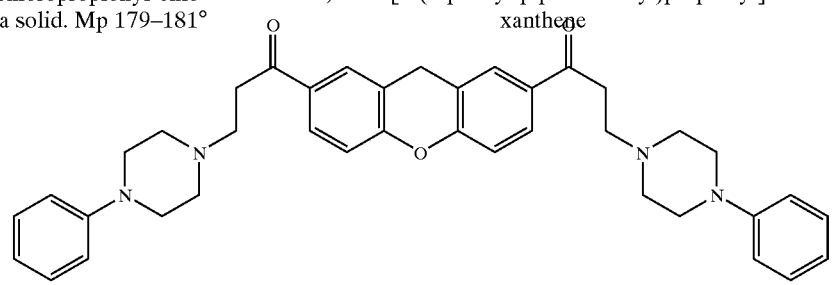

Prepared from compound 17 and 4-phenyl-piperazine according to General Procedure C to give a solid. Mp 206–208° C. $^1$H NMR (CDCl$_3$, 400 MHz) δ7.91–7.86 (m 4H), 7.29 (t, J=10 Hz, 4H), 7.14 (d, J=10 Hz, 2H), 6.96–6.91 (m, 6H), 4.16 (s, 2H), 3.51–3.46 (m, 12H), 3.38–3.10 (m, 12H). Anal. (C$_{39}$H$_{42}$N$_4$O$_3$.).

EXAMPLE 40

2,7-Bis-{3-[4-(3-trifluoromethyl-phenyl)-piperazin-1-yl]-propionyl}-xanthene

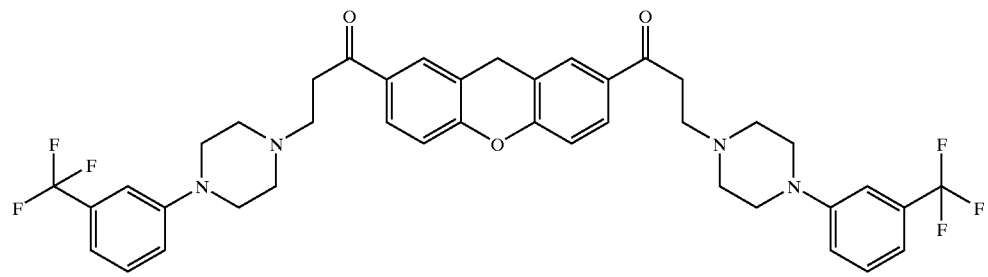

Prepared from compound 17 and 4-(3-trifluoromethyl-phenyl)-piperazine according to General Procedure C to give a solid. Mp 155–157° C. $^1$H NMR (CDCl$_3$, 400 MHz) δ7.92–7.88 (m, 4H), 7.39 (t, J=8.8 Hz, 2H), 7.17–7.13 (m, 6H), 7.07 (dd, J=8.8, 2.0 Hz, 2H), 4.17 (s, 2H), 3.53–3.04 (m, 24H). Anal. (C$_{41}$H$_{40}$F$_6$N$_4$O$_3$).

EXAMPLE 41

2,7-Bis-{3-[4-(3-trifluoromethyl-phenyl)-piperazin-1-yl]-propionyl}-xanthen-9-one

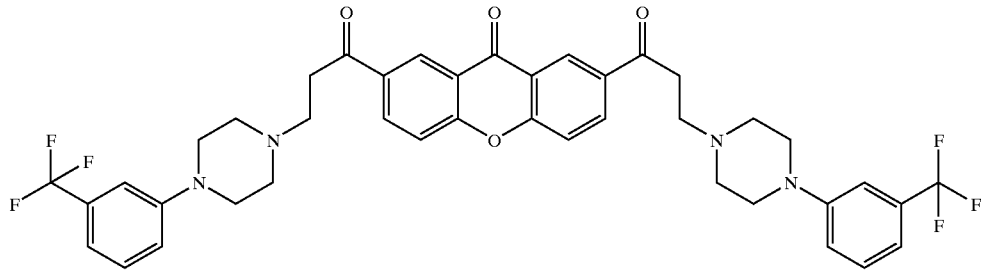

Prepared from compound 17 and 4-(3-trifluoromethyl-phenyl)-piperazine according to General Procedure C to give a solid. Mp 166–167° C. $^1$H NMR (CDCl$_3$, 400 MHz) δ8.95 (d, J=2.2 Hz, 2H), 8.42 (dd, J=8.8, 2.2 Hz, 2H), 7.63 (d, J=8.8 Hz, 2H), 7.36 (t, J=7.8 Hz, 2H), 7.12–7.06 (m, 6H), 3.60–2.80 (m, 24H). Anal. (C$_{41}$H$_{38}$F$_6$N$_4$O$_4$-0.6H$_2$O).

EXAMPLE 42

2,7-Bis-[3-(4-phenyl-piperazin-1-yl)-propionyl]-xanthen-9-one

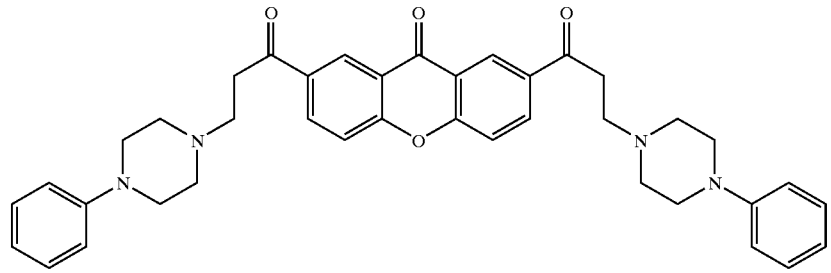

Prepared from compound 17 and 4-phenyl-piperazine according to General Procedure C to give a solid. Mp 199–201° C. $^1$H NMR (CDCl$_3$, 400 MHz) δ8.91 (d, J=2.2 Hz, 2H), 8.40 (dd, J=8.8, 2.2 Hz, 2H), 7.61 (d, J=8.8 Hz, 2H), 7.32–7.23 (m, 4H), 6.98–6.90 (m, 6H), 3.93–3.23 (m, 24H). Anal. (C$_{39}$H$_{40}$N$_4$O$_4$).

EXAMPLE 43

1,9-Bis{N-[4-(4-fluoro-phenyl)-piperazine-carbamoyl]}-10,10-dioxo-phenoxathiin

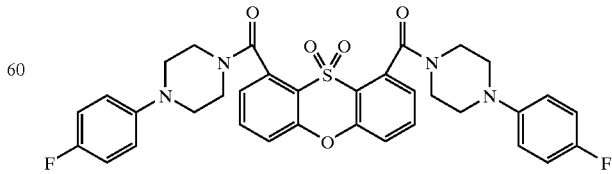

Prepared from compound 22 and (4-fluoro-phenyl)-piperazine according to General Procedure B to give a white solid. Mp 180–183° C. ¹H NMR (TFA-d₃, 400 MHz) δ7.77 (t, J=7,6, 8.6 Hz, 1H), 7.57 (d, J=7.6 Hz, 1H), 7.50 (dd, J=3.7, 8.7 Hz, 2H), 7.35 (d, J=5.3 Hz, 1H), 7.16 (t, J=7.8, 8.6 Hz, 1H), 5.00–5.15 (m, 1H), 4.02–4.18 (m, 1H), 3.62–3.98 (m, 5H), 3.40–3.55 (m, 1H).

EXAMPLE 44

1,9-Bis-{N-[4-(4-trifluoromethyl-phenyl)-piperazine]carbamoyl}-10,10-dioxo-phenoxathiin

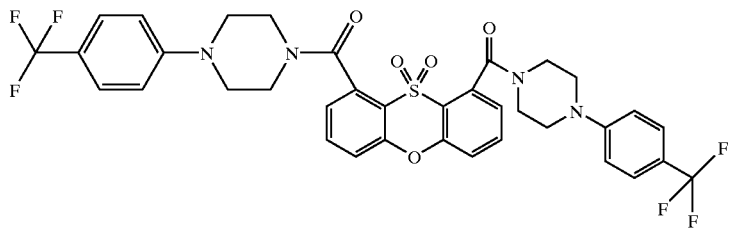

Prepared from compound 22 and 4-(4-trifluoromethyl-phenyl)-piperazine according to General Procedure B to give a white solid. Mp 80–85° C. ¹H NMR (TFA-d₃, 400 MHz) δ 7.79–7.87 (m, 3H), 7.73 (d, J=8.6 Hz, 1H), 7.62 (d, J=8.6 Hz, 1H), 7.43 (d, J=7.6 Hz, 1H), 4.17 (t, J=12 Hz, 1H), 3.80–4.06 (m, 6H), 3.64 (d, J=12 Hz, 1H).

EXAMPLE 45

1,9-Bis{N-[4-(4-hydroxy-phenyl)-piperazine]carbamoyl}-10,10-dioxo-phenoxathiin

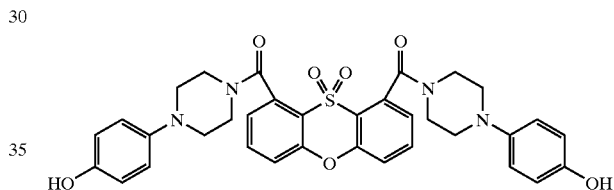

Prepared from compound 22 and N-(4-hydroxy-phenyl)-piperazine according to General Procedure B to give a white solid. LRMS (EI−), M−1=637.

EXAMPLE 46

1,9-Bis{N-[4-(pyridin-4-yl)-piperazine]carbamoyl}-10,10-dioxo-phenoxathiin

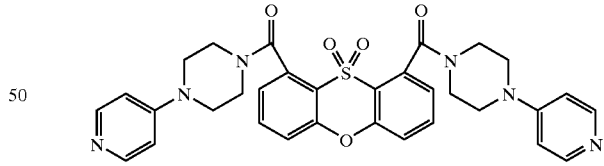

Prepared from compound 22 and N-(pyridin-4-yl)-piperazine according to General Procedure B to give a white solid. LRMS (EI+), M+1=611.

EXAMPLE 47

1,9-Bis-[N-(3-phenpropyl)carbamoyl]-10,10-dioxo-phenoxathiin

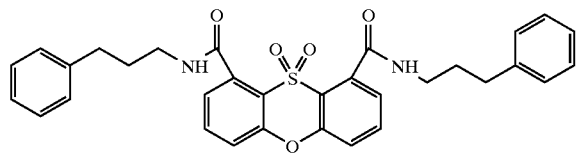

Prepared from compound 22 and 3-phenpropyl amine according to General Procedure B to give a white solid. LRMS (EI−), M−1=551.

EXAMPLE 48

1,9-Bis{N-[2-(2,4-dichlorophenyl)ethyl]carbamoyl}-10,10-dioxo-phenoxathiin

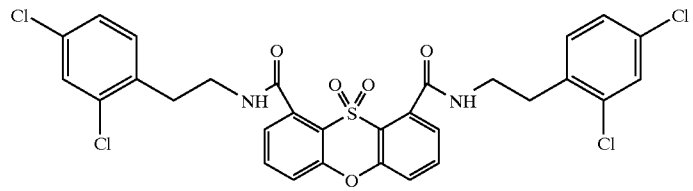

Prepared from compound 22 and 2-(2,4-dichloro)ethyl amine according to General Procedure B to give a white solid. LRMS (EI−), M−1=661.

EXAMPLE 49

1,9-Bis{N-[2-(pyrrolidin-1-yl)ethyl]carbamoyl}-10,10-dioxo-phenoxathiin

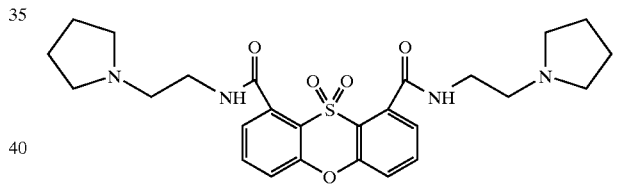

Prepared from compound 22 and ethyl pyrrolidine according to General Procedure B to give a white solid. LRMS (EI+), M+1=513.

EXAMPLE 50

1,9-Bis{N-[2-(thiophen-2-yl)ethyl]carbamoyl}-10,10-dioxo-phenoxathiin

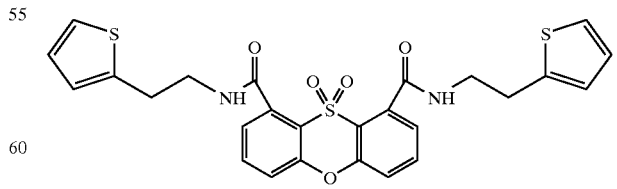

Prepared from compound 22 and 2-aminothiophene according to General Procedure B to give a white solid. LRMS (EI−), M−1=535.

EXAMPLE 51

1,9-Bis{N-[3-(morpholin-4-yl)-propyl]carbamoyl}-10,10-dioxo-phenoxathiin

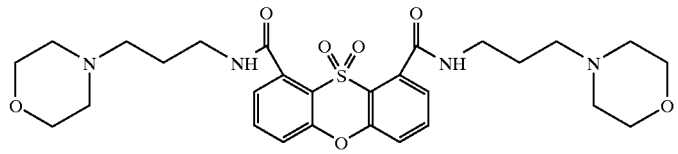

Prepared from compound 22 and 3-(morpholin-4-yl)-propyl amine according to General Procedure B to give a white solid. LRMS (EI+), M+1=573.

EXAMPLE 52

1,9-Bis {N-[2-(3,5-dimethoxyphenyl)ethyl] carbamoyl}-10,10-dioxo-phenoxathiin

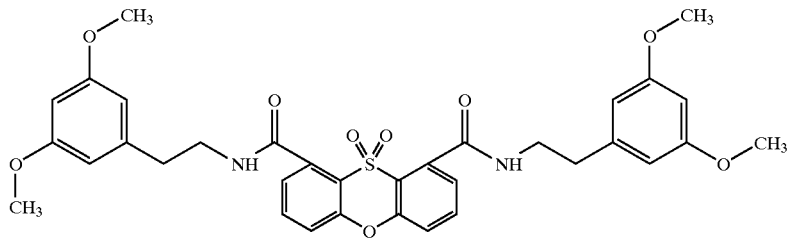

Prepared from compound 22 and 2-(3,5-dimethoxyphenyl)-ethyl amine according to General Procedure B to give a white solid. LRMS (EI−), M−1=643.

EXAMPLE 53

3,9-Bis[4-(methylphenylamino)butyryl]fluoranthene

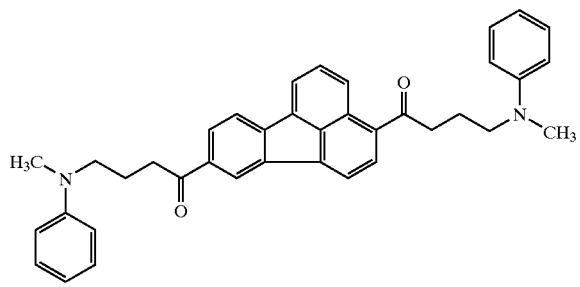

This compound was prepared through an intermediate of 3,9-bis(4-chlorobutyryl)fluoranthene, which was available by acylation of fluoranthene 11 with 4-chloro-butyryl chloride. See Albrecht et al., *J. Med. Chem.*, 17, 1150–1156 (1974). Reaction of 3,9-bis(4-chlorobutyryl)fluoranthene with methylphenylamine according to General Procedure C gave the desired product as a solid. LRMS (ES+), M+1= 552.8.

EXAMPLE 54

3,9-Bis[4-(1-pyrrolo)butyryl]fluoranthene

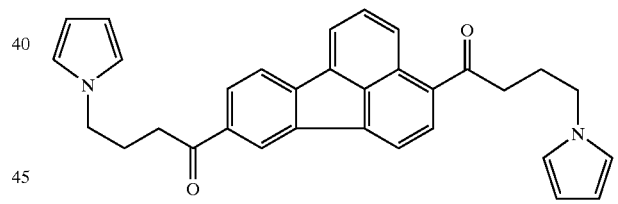

Reaction of 3,9-bis(4-chlorobutyryl)fluoranthene (as described above in Example 53) with pyrrole according to General Procedure C gave the desired product as a solid. LRMS (ES+), M+1=473.6.

EXAMPLE 55

3,9-Bis[3-(1-pyrrolo)propionyl]fluoranthene

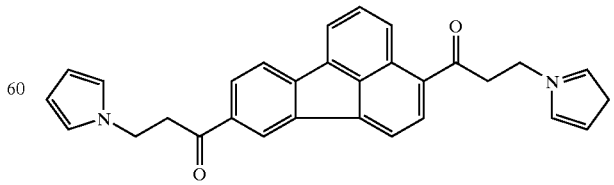

This compound was prepared through an intermediate of 3,9-bis(4-chloropropionyl)fluoranthene, which was available by acylation of fluoranthene 11 with 3-chloro-propyl chloride. See Albrecht et al., *J. Med. Chem.*, 17, 1150–1156 (1974). Reaction of 3,9-bis(4-chloropropionyl)fluoranthene with pyrrole according to General Procedure C gave the desired product as a solid. LRMS (ES+), M+1=485.1.

EXAMPLE 56

9-Oxo-9H-fluorene-2,7-bis-(phenethyl-amide)

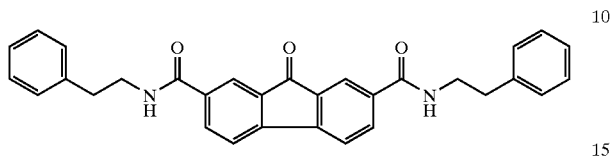

Prepared by reacting 9-fluorenone-2,7-diacyl chloride with phenethylamine using the procedure described in example 16 to provide the desired compound in solid. Mp 327–329° C. $^1$H NMR (DMSO-$d_6$, 400 MHz) δ8.82 (s, 1H), 8.12 (m, 1H), 8.00 (m, 1H), 7.28 (m, 5H), 3.53 (m, 2H), 2.88 (m, 2H). LRMS: (ES−) M−1=473.

EXAMPLE 57

9-Oxo-9H-fluorene-2,7-bis-(3,4-dichloro-benzylamide)

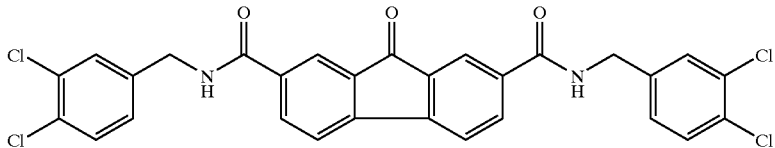

Prepared by reacting 9-fluorenone-2,7-diacyl chloride with 3,4-dichloro-benzylamine using the procedure described in example 16 to provide the desired compound in solid form. Mp 265–267° C. $^1$H NMR (DMSO-$d_6$, 400 MHz) δ9.34 (m, 1H), 8.19 (m, 2H), 8.03 (d, J=9 Hz, 1H), 7.61 (m, 2H), 7.35 (d, J=9 Hz, 1H), 4.50 (d, J=6 Hz, 1H). LRMS: (ES−) M−1=583.

EXAMPLE 58

9-Oxo-9H-fluorene-2,7-bis-(3,4-dihydroxy-benzylamide)

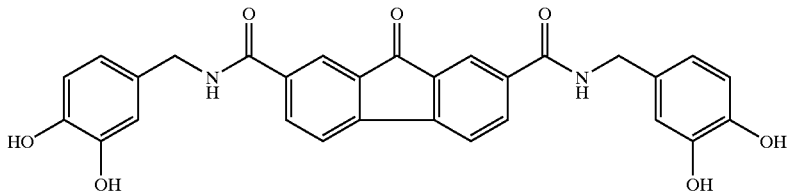

Prepared reacting 9-fluorenone-2,7-diacyl chloride with 4-aminomethyl-benzene-1,2-diol using the procedure described in example 16 to provide the desired compound in solid form. Mp 160–163° C. $^1$H NMR (DMSO-d$_6$, 400 MHz) δ8.18 (m, 2H), 8.02 (m, 1H), 6.75 (s, 1H), 6.67 (m, 2H), 4.43 (s, 2H). LRMS: (ES−) M−1=509.

EXAMPLE 59

2,7-Bis-{3-[1-(4-fluoro-phenyl)-piperazine-1-yl]-propionyl}-xanthen-9-one

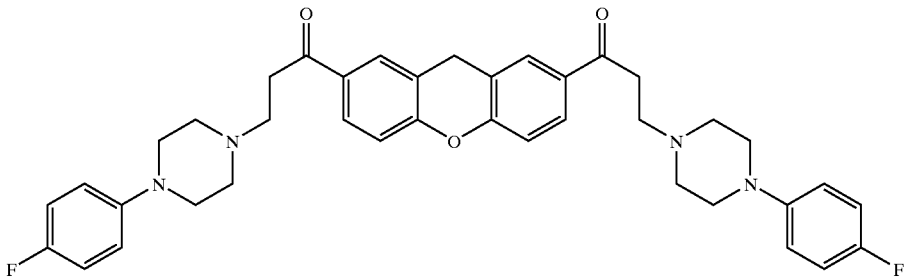

Prepared from compound 17 and 1-(4-fluoro-phenyl)-piperazine according to General Procedure C to give a yellow solid. Mp 207–209° C. $^1$H NMR (CDCl$_3$, 400 MHz) δ7.86–7.83 (m, 4H), 7.11 (d, J=8.1 Hz, 2H), 6.98–6.92 (m, 4H), 6.89–6.84 (m, 4H), 4.15 (s, 2H), 3.19 (t, J=7.1 Hz, 4H), 3.14–3.11 (m, 8H), 2.90 (t, J=7.1 Hz, 4H), 2.87–2.67 (m, 8H). LRMS: (ES+) M+1=651.

EXAMPLE 60

2,7-Bis-{3-[1-(3-chloro-phenyl)-piperazine-1-yl]-propionyl}-xanthen-9-one

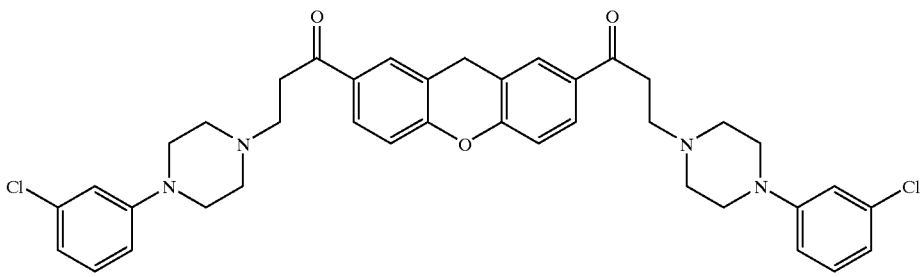

Prepared from compound 17 and 1-(3-chloro-phenyl)-piperazine according to General Procedure C to give a solid. Mp 182–185° C. $^1$H NMR (CDCl$_3$, 400 MHz) δ7.86 (m, 4H), 7.17–7.11 (m, 4H), 6.86–6.76 (m, 6H), 4.16 (s, 2H), 3.20–3.17 (m, 12H), 2.89 (t, J=7.1 Hz, 4H), 2.67–2.65 (m, 8H). LRMS: (ES+) M+1=684.

Biological Testing; Enzyme Assays
PARG Enzymatic Assay

The potency of PARG inhibition was determined in a PARG enzymatic assay. For each compound, various doses were used to inhibit the PARG reaction. A dose responsible curve was generated to determine the IC$_{50}$ value and the concentration (in μM) required to achieve 50% inhibition of the reaction.

The term "inhibition," in the context of enzyme inhibition, relates to reversible enzyme inhibition such as competitive, uncompetitive, and noncompetitive inhibition. This can be experimentally distinguished by the effects of the inhibitor on the reaction kinetics of the enzyme, which may be analyzed in terms of the basic Michaelis-Menten rate equation. Competitive inhibition occurs when the inhibitor can combine with the free enzyme in such a way that it competes with the normal substrate for binding at the active site. A competitive inhibitor reacts reversibly with the enzyme to form an enzyme-inhibitor complex [EI], analogous to the enzyme-substrate complex:

$$E+I=EI$$

Following the Michaelis-Menten formalism, we can define the inhibitor constant, K$_i$, as the dissociation constant of the enzyme-inhibitor complex:

$$K_i = \frac{[E][I]}{[EI]}$$

Thus, in accordance with the above and as used herein, K$_i$ is essentially a measurement of affinity between a molecule, and its receptor, or in relation to the present invention, between the present inventive compounds and the enzyme to be inhibited. It should be noted that IC$_{50}$ is a related term used when defining the concentration or amount of a compound that is required to cause a 50% inhibition of the target enzyme.

The PARG assay consisted of (a) preparation of 3H-labeled radioactive PARG as substrate, (b) purification of recombinant PARG, (c) incubation of the compound with the PARG reaction, (d) separation of the product by absorption to glass fiber filter and quantifying the radioactivity of ADP-ribose by scintillation counting.

(a) Preparation of 3H-poly-(ADP-ribose) Polymer 3H-labeled poly-(ADP-ribose) was made by mixing labeled and unlabeled PAR. Labeled PAR was synthesized in a reaction of 50 mM Tris-HCl (pH 8.0), 4 mM MgCl$_2$, 0.8 μg/mL activated DNA, 3 μM NAD, NEN 3H-NAD (0.1 mCi/mL), 0.8 μl/mL and 1.4 μl/mL Trevigen PARP. The reaction was incubated at room temperature for 60 min, then dialyzed to remove unincorporated 3H NAD using a MWCO 7000 dialysis cassette in 50 mM Phosphate buffer (pH 7.1) at 5° C. over night. Buffer was changed and dialysis continued for 2 h in the morning. The resulting 3H PAR gave 80,000 DPM/10 μL by scintillation counting.

Unlabeled PAR was synthesized in a reaction that consisted of 50 mM Tris-HCl (pH 8.0), 4 mM $MgCl_2$, 0.8 μg/mL activated DNA, 150 μM NAD, and 1.9 μl/mL Trevigen PARP. The reaction was incubated at room temperature for 60 min, and dialyzed to remove unincorporated NAD in a MWCO 7000 cassette using 50 mM Phosphate buffer (pH 7.1) over night at 50° C. Buffer was changed and dialysis continued for 2 h in the morning. The OD260 of synthesized PAR is 0.2–0.03.

The final PAR mix is made by combining 3H-PAR and PAR synthesized @ 150 μM NAD so that the OD260= 0.2–0.3 and the DPM/10 μL=10,000 DPM (SA=0.45 Ci/mmole). EDTA was added to 1 mM.

(b) Expression and Purification of Recombinant PARG

A cDNA fragment encoding the carboxy terminal part of human PARG from amino acid 378 to 976 was amplified by polymerase chain reaction with human thymus cDNA (Clontech, Palo Alto, Calif.) as a template and a pair of primers with the sequences of 5'-GGGAATTCATGAATGATTTAAATGCTAAA-3' and 5'-CCCTCGAGTCAGGTCCCTGTCCTTTGCCC-3'. The primers contained the restriction enzyme sites EcoRI and XhoI. The PCR amplified PARG DNA fragment was digested with EcoRI and XhoI, and then ligated to the same sites in pGEX-4T1 plasmid (acquired from Pharmacia/ Upjohn Co., Kalamazoo, Mich.) to create pGEX-PARG by using standard molecular biology procedure. The pGEX-PARG was transformed into *E. coli* strain BL21 for expressing the recombinant protein that has a glutathione-S-transferase at the amino terminus and fused in frame with PARG at the carboxy terminus. The recombinant protein was expressed and purified using glutathione-sephadex 4B beads according to the standard methodology.

(c) PARG Reaction

A range of potential PARG inhibitors at final concentrations of 200.0 to 0.1 μM were tested, each point done in triplicate. The compounds were dissolved in DMSO resulting in a final DMSO concentration of 5.0%. The reaction was carried out in a volume of 0.1 mL. PARG enzyme was added to a concentration of 0.05 μL/mL to microtiter plates containing approximately 10 μM 3H-labeled poly-(ADP-ribose) in 50 mM Phosphate buffer (pH 7.1), 5 mM B-mercaptoethanol. The reaction was incubated at 23° C. for 10 min. and was stopped with the addition of TCA to a final concentration of 10%.

(d) Quantifying PARG Activities

Enzyme activity was measured by the disappearance of substrate, [poly-(ADP-ribose) polymer], which was quantified as the loss of glass fiber filter adsorbed radioactivity. The reaction was harvested onto Millipore GFC96 well filter plates using the Packard Cell Harvestor. The plates were washed three times with 70% ethanol, air dried, and the radioactivity was measured by scintillation counting.

The testing results of the compounds using the PARG assay are summarized in Table 1.

TABLE 1

| Ex. # | $IC_{50}$ (μM) |
|---|---|
| 1 | 13.5 |
| 2 | 11.3 |

TABLE 1-continued

| Ex. # | $IC_{50}$ (μM) |
|---|---|
| 3 | 21 |
| 4 | 18.9 |
| 5 | 11.2 |
| 6 | 10 |
| 7 | 45.6 |
| 8 | 17.1 |
| 9 | 46.6 |
| 10 | 27.1 |
| 11 | 7.9 |
| 12 | 18.3 |
| 13 | 4.3 |
| 14 | 47.7 |
| 15 | 24.9 |
| 16 | 1.7 |
| 17 | 21.8 |
| 18 | 6 |
| 19 | 75 |
| 20 | 40.1 |
| 21 | 65.6 |
| 22 | 17.1 |
| 23 | 35.2 |
| 24 | 57 |
| 25 | 28.6 |
| 26 | 100 |
| 27 | 100 |
| 28 | 11.1 |
| 29 | 29 |
| 30 | 21.2 |
| 31 | 30.4 |
| 32 | 21.1 |
| 33 | 45.5 |
| 34 | 31.2 |
| 35 | 15.1 |
| 36 | 106 |
| 37 | 17 |
| 38 | 17 |
| 39 | 7.1 |
| 40 | 10.6 |
| 41 | 17.5 |
| 42 | 100 |
| 43 | 5.7 |
| 44 | 12 |
| 45 | 37.9 |
| 46 | 28.4 |
| 47 | 100 |
| 48 | 38.7 |
| 49 | 9.9 |
| 50 | 11.5 |
| 51 | 9.6 |
| 52 | 31.6 |
| 53 | 11.8 |
| 54 | 5.4 |
| 55 | 27.3 |
| 56 | 22 |
| 57 | 15 |
| 58 | 10 |
| 59 | 2.9 |
| 60 | 1.1 |

What is claimed is:

1. A compound of the Formula VII:

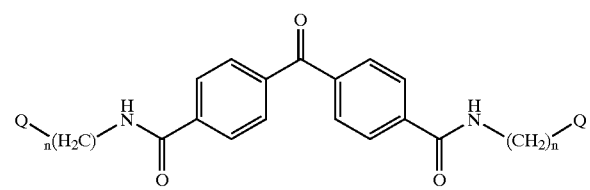

VII wherein:

n is 1 to 3; and

Q is a substituted or unsubstituted aryl or heteroaryl;

or a pharmaceutically acceptable prodrug of said compound, pharmaceutically active metabolite of said compound, or pharmaceutically acceptable salt of said compound or metabolite.

2. A compound, prodrug, metabolite, or salt according to claim 1 selected from:

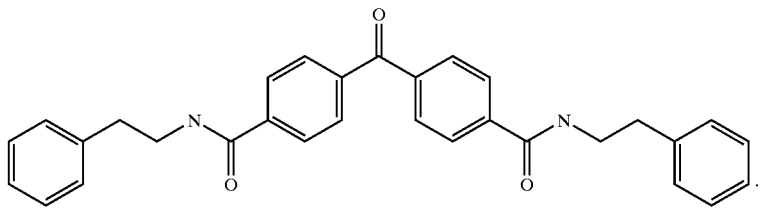

3. A pharmaceutical composition comprising a pharmaceutically acceptable carrier and a compound of formula VII:

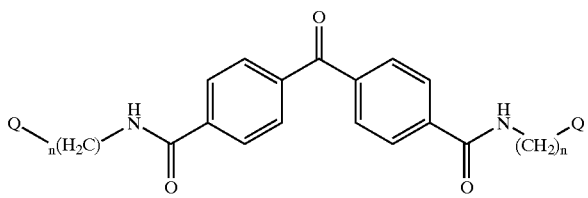

wherein:

n is 1 to 3; and

Q is a substituted or unsubstituted aryl or heteroaryl;

or a pharmaceutically acceptable prodrug of said compound, pharmaceutically active metabolite of said compound, or pharmaceutically acceptable salt of said compound or metabolite.

4. The pharmaceutical composition according to claim 3 selected from:

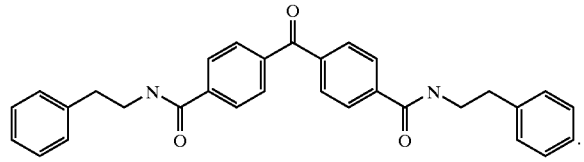

5. The composition according to claim 3, wherein said composition is administered as a sterile solution, suspension or emulsion, in a single or divided dose.

6. The composition according to claim 3, wherein said composition is administered as a capsule or tablet containing a single or divided dose of said compound.

7. The composition according to claim 3, wherein the composition is a solid implant.

8. The composition according to claim 3, wherein the carrier comprises a biodegradable polymer.

9. The composition according to claim 8, wherein the biodegradable polymer releases the compound of formula VII over a prolonged time.

10. A method of modulating or inhibiting PARG by administering a compound of Formula VII according to claim 1, or a pharmaceutically acceptable prodrug, pharmaceutically active metabolite, or pharmaceutically acceptable salt of such compound or metabolite thereof, to treat diseases and disorders selected from acute pain, arthritis, atherosclerosis, cachexia, cardiovascular disorders, chronic pain, degenerative diseases, diabetes, head trauma, hyperglycemia, immune senescence, inflammatory bowel disorders, ischemia, macular degeneration, muscular dystrophy, tissue damage resulting from ischemia and reperfusion injury, neurological disorders and neurodegenerative diseases, neuronal tissue damage or disease, neuropathic pain, nervous insult, osteoarthritis, osteoporosis, peripheral nerve injury, renal failure, resuscitated hemorrhagic shock, retinal ischemia, septic shock, skin aging, vascular stroke, diseases or disorders relating to lifespan or proliferative capacity of cells, and diseases or disease conditions induced or exacerbated by cellular senescence.

11. The method according to claim 10 wherein the diseases or conditions are selected from diabetes, head trauma, inflammatory bowel disorders, ischemia, tissue damage resulting from ischemia and reperfusion injury, neurological disorders and neurodegenerative diseases, neuronal tissue damage disease, neuropathic pain, nervous insult, peripheral nerve injury, retinal ischemia, vascular stroke, and diseases or disorders relating to lifespan or proliferative capacity of cells.

12. The method according to claim 11 wherein the disease or condition is tissue damage resulting from ischemia and reperfusion injury.

13. A compound of the Formula VIII:

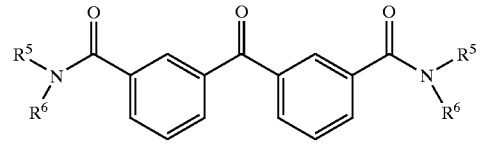

wherein:

$R^5$ is hydrogen, and $R^6$ is a substituted or unsubstituted lower alkyl, lower alkenyl, heterocycloalkyl, alkoxy, aryloxy, alkylamino, arylamino, or R⁵ and R⁶ are taken together to form a substituted or unsubstituted five to seven membered heterocyclic ring that contains 1–3 heteroatoms of O, N, or S;

or a pharmaceutically acceptable prodrug of said compound, pharmaceutically active metabolite of said compound, or pharmaceutically acceptable salt of said compound or metabolite.

14. A compound, prodrug, metabolite, or salt according to claim 13, wherein:

R⁵ is hydrogen, and R⁶ is a substituted or unsubstituted lower alkyl, or R⁵ and R⁶ are taken together to form a substituted or unsubstituted six membered heterocyclic ring that contains 1–2 heteroatoms of N.

15. A compound, prodrug, metabolite, or salt according to claim 14 selected from:

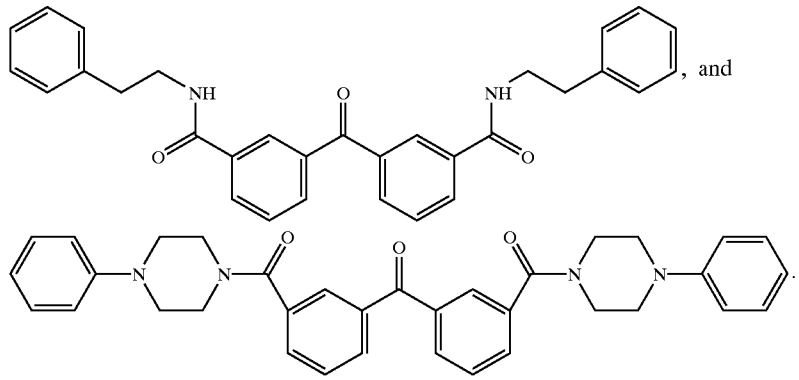

16. A pharmaceutical composition comprising a pharmaceutically acceptable carrier and a compound of formula VIII:

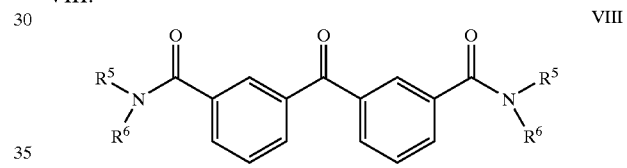

wherein:

R⁵ is hydrogen, and R⁶ is a substituted or unsubstituted lower alkyl, lower alkenyl, heterocycloalkyl, alkoxy, aryloxy, alkylamino, arylamino, or R⁵ and R⁶ are taken together to form a substituted or unsubstituted five to seven membered heterocyclic ring that contains 1–3 heteroatoms of O, N, or S;

or a pharmaceutically acceptable prodrug of said compound, pharmaceutically active metabolite of said compound, or pharmaceutically acceptable salt of said compound or metabolite.

17. The pharmaceutical composition according to claim 16, wherein:

R⁵ is hydrogen, and R⁶ is a substituted or unsubstituted lower alkyl, or R⁵ and R⁶ are taken together to form a substituted or unsubstituted six membered heterocyclic ring that contains 1–2 heteroatoms of N.

18. The pharmaceutical composition according to claim 17 selected from:

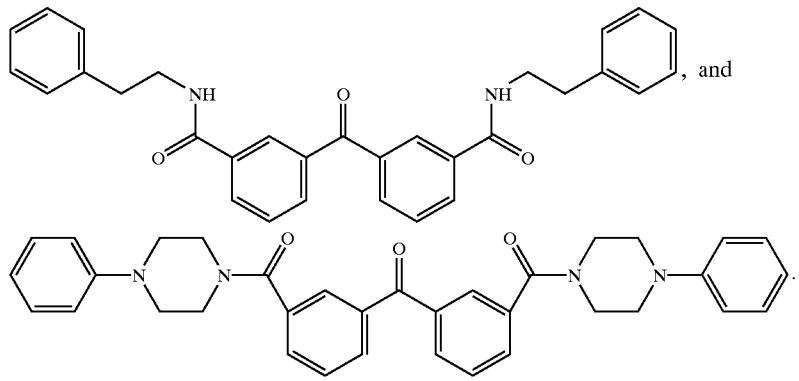

19. The composition according to claim 16, wherein said composition is administered as a sterile solution, suspension or emulsion, in a single or divided dose.

20. The composition according to claim 16, wherein said composition is administered as a capsule or tablet containing a single or divided dose of said compound.

21. The composition according to claim 16, wherein the composition is a solid implant.

22. The composition according to claim 16, wherein the carrier comprises a biodegradable polymer.

23. The composition according to claim 22, wherein the biodegradable polymer releases the compound of formula VIII over a prolonged time.

24. A method of modulating or inhibiting PARG by administering a compound of Formula VIII according to claim 13, or a pharmaceutically acceptable prodrug, pharmaceutically active metabolite, or pharmaceutically acceptable salt of such compound or metabolite thereof, to treat diseases and disorders selected from acute pain, arthritis, atherosclerosis, cachexia, cardiovascular disorders, chronic pain, degenerative diseases, diabetes, head trauma, hyperglycemia, immune senescence, inflammatory bowel disorders, ischemia, macular degeneration, muscular dystrophy, tissue damage resulting from ischemia and reperfusion injury, neurological disorders and neurodegenerative diseases, neuronal tissue damage or disease, neuropathic pain, nervous insult, osteoarthritis, osteoporosis, peripheral nerve injury, renal failure, resuscitated hemorrhagic shock, retinal ischemia, septic shock, skin aging, vascular stroke, diseases or disorders relating to lifespan or proliferative capacity of cells, and diseases or disease conditions induced or exacerbated by cellular senescence.

25. The method according to claim 24 wherein the diseases or conditions are selected from diabetes, head trauma, inflammatory bowel disorders, ischemia, tissue damage resulting from ischemia and reperfusion injury, neurological disorders and neurodegenerative diseases, neuronal tissue damage disease, neuropathic pain, nervous insult, peripheral nerve injury, retinal ischemia, vascular stroke, and diseases or disorders relating to lifespan or proliferative capacity of cells.

26. The method according to claim 25 wherein the disease or condition is tissue damage resulting from ischemia and reperfusion injury.

* * * * *